United States Patent
Wu et al.

(10) Patent No.: US 12,178,593 B2
(45) Date of Patent: *Dec. 31, 2024

(54) APPARATUS FOR EXAMINING BRAIN INJURY, METHOD OF MAKING AND METHOD OF USING THE SAME

(71) Applicant: Villanova University, Villanova, PA (US)

(72) Inventors: Qianhong Wu, Malvern, PA (US); Ji Lang, Taiyuan (CN)

(73) Assignee: Villanova University, Villanova, PA (US)

( * ) Notice: Subject to any disclaimer, the term of this patent is extended or adjusted under 35 U.S.C. 154(b) by 203 days.

This patent is subject to a terminal disclaimer.

(21) Appl. No.: 18/067,796

(22) Filed: Dec. 19, 2022

(65) Prior Publication Data

US 2023/0139872 A1 May 4, 2023

Related U.S. Application Data

(63) Continuation of application No. 16/256,308, filed on Jan. 24, 2019, now Pat. No. 11,559,245.

(Continued)

(51) Int. Cl.
*A61B 5/00* (2006.01)
*A61B 5/16* (2006.01)
(Continued)

(52) U.S. Cl.
CPC ............. *A61B 5/4064* (2013.01); *A61B 5/16* (2013.01); *G09B 23/303* (2013.01); *G09B 23/32* (2013.01);
(Continued)

(58) Field of Classification Search
None
See application file for complete search history.

(56) References Cited

U.S. PATENT DOCUMENTS 9,552,747 B1 1/2017 Lytle
10,359,348 B1 7/2019 Lytle
(Continued)

FOREIGN PATENT DOCUMENTS

WO 2004110309 A2 12/2004

OTHER PUBLICATIONS

Wu, et al., "A Biphasic Approach for the Study of Lift Generation in Soft Porous Media," Physics of Fluids 29, American Institute of Physics, AIP Publishing, Apr. 28, 2017, pp. 043602-1 through 043602-15.

(Continued)

*Primary Examiner* — James B Hull
(74) *Attorney, Agent, or Firm* — Duane Morris LLP

(57) ABSTRACT

A test apparatus or system for testing impact induced brain trauma a method of making and a method using the same are provided. The system includes a head model, which includes a skull component, a brain component, and a fluid component. The skull component has a wall defining an interior chamber. The brain component includes a gel material and is disposed within the interior chamber. The fluid component is disposed inside the interior chamber. The system may also include a fluid tank fluidly coupled with the skull component and configured to provide the fluid component into the interior chamber. The head model may further include a layer of porous media disposed between the brain component and the interior wall surface of the skull component. The system may include at least one impact element for providing an impact on the head model. The impact is translational or rotational or both.

20 Claims, 17 Drawing Sheets

Related U.S. Application Data

(60) Provisional application No. 62/621,854, filed on Jan. 25, 2018.

(51) Int. Cl.
    *G09B 23/30*     (2006.01)
    *G09B 23/32*     (2006.01)
    *A61B 5/369*     (2021.01)

(52) U.S. Cl.
    CPC ......... *A61B 5/369* (2021.01); *A61B 2576/026* (2013.01)

(56) References Cited

U.S. PATENT DOCUMENTS

| | | |
|---|---|---|
| 11,559,245 B2 | 1/2023 | Wu et al. |
| 2003/0186203 A1 | 10/2003 | Aboud |
| 2017/0261416 A1 | 9/2017 | Wu et al. |
| 2018/0172551 A1 | 6/2018 | Pradeep |

OTHER PUBLICATIONS

Zhu, et al., "On the Examination of the Darcy Permeability of Soft Fibrous Porous Media; New Correlations," Chemical Engineering Science 173 (2017), Aug. 24, 2017, pp. 525-536.

Gacka, et al., "From Red Cells to Soft Lubrication, an Experimental Study of Lift Generation Inside a Compressible Porous Layer," J. Fluid Mech. (2017), vol. 818, pp. 5-25, Camberidge University Press, Apr. 4, 2017.

Lang, et al., "Exact and Approximate Solutions for Transient Squeezing Flow," Physics of Fluids 29, AIP Publishing, Aug. 4, 2017, pp. 103606-1 through 103606-9.

Bieszk, et al., "Brain Modeling to Mimic Functionality Studies of Cerebrospinal Fluid", Proceedings of the National Conference on Undergraduate Research (NCUR), Apr. 3-5, 2014, 6 pages.

Mehrabian, et al., Dual-Porosity Poroviscoelasticity and Quantitative Hydromechanical Characterization of the Brain Tissue with Experimental Hydrocephalus Data, Journal of Theoretical Biology, 384 (2015) pp. 19-32, Aug. 13, 2015.

Nicholson, Charles, Diffusion and Related Transport Mechanisms in Brain Tissue, Institute of Physics Publishing, Reports on Progress in Physics 64 (2001) pp. 815-884, Jun. 26, 2001.

Shafieian, et al., "Development of a Constitutive Model for Brain Tissue Under Multiaxial Loading", IRC-12-56, IRCOBI Conference 2012, pp. 467-473.

Sogbesan, Eyitejumade A., "Design and Analysis of Blast Induced Traumatic Brain Injury Mechanism Using a Surrogate Headform: Instrumentation and Outcomes", University of Nebraska, Apr. 2, 2011, pp. 1-103.

Tawse, Kristen, Cerebrospinal Fluid-Tissue Interactions in the Human Brain, REU Summer Program, Chicago, IL, Jun. 5, 2006, pp. 1-13.

Linge, et al., "CSF Flow Dynamics at the Craniovertebral Junction Studied with an Idealized Model of the Subarachnoid Space and Computational Flow Analysis", AJNR Am J. Neuroradiol 31:185-92, Jan. 2010, pp. 185-192.

Furlan, et al, "CSF Flow Characterization within a Model of the Cerebral Ventricular System Using Particle Image Velocimetry", FLUVISU12—12th French Congress on Visualization in Fluid Mechanics, Jul. 1-4, 2008, pp. 1-19, Nice, France.

Franceschini, et al., "Brain Tissue Deforms Similarly to Filled Elastomers and Follows Consolidation Theory", Science Direct, Journal of the Mechanics and Physics of Solids, 54 (2006), May 3, 2006, pp. 2592-2620.

Margulies, et al., "Physical Model Simulations of Brain Injury in the Primate", J. Biomechanics, vol. 23, No. 8, pp. 823-836, 1990.

Gevertz, et al., "A Novel Three-Phase Model of Brain Tissue Microstructure", PLOS Computational Biology 4(8), Aug. 15, 2008, pp. 1-19, vol. 4, Issue 8, e1000152.

Capek, Tyler, "Modeling the Human Brain's Major Structures and White Matter Connectivity Using Magnetic Resonance and Diffusion Tensor Imaging", Proceeding of the National Conference on Undergraduate Research (NCUR), Apr. 11-13, 2013, pp. 634-640.

Xi, et al., "Mechanisms of Brain Injury After Intracerebral Haemorrhage", Lancet Neurol 2006; pp. 53-63, vol. 5, Jan. 2006.

Meaney, et al., "The Mechanics of Traumatic Brain Injury: A Review of What We Know and What We Need to Know for Reducing Its Societal Burden", Journal of Biomechanical Engineering, Feb. 2014, pp. 021008-1 through 021008-14, vol. 136.

Holbourn, et al, "Mechanics of Head Injuries", The Lancet, Oct. 9, 1943, pp. 438-441.

Hossain, S.G.M., "Material Modeling and Analysis for the Development of a Realistic Blast Headform", Mechanical (and Materials) Engineering—Dissertations, Theses, and Student Research, University of Nebraska—Lincoln, Aug. 2010, pp. 1-125.

Bateman, Jen, "Manufacture of a Prototype for Functionality Studies of Cerebrosinal Fluid", Research Experience for Undergraduates 2014, National Science Foundation Grant, Jun. 1-Aug. 8, 2014, pp. 1-9.

Kertzscher, et al., "In Vitro Study of Cerebrospinal Fluid Dynamics in a Shaken Basal Cistern After Experimental Subarachnoid Hemorrhage", PLoS ONE 8(8), Aug. 1, 2012, pp. 1-10, vol. 7, Issue 8, e41677.

Ivarsson, et al., "Influence of the Lateral Ventricles and Irregular Skull Base on Brain Kinematics due to Sagittal Plane Head Rotation", Transcations of the ASME, vol. 124, pp. 422-431, Aug. 2002.

Greenwald, et al., "Head Impact Severity Measures for Evaluating Mild Traumatic Brain Injury Risk Exposure", Neurosurgery 62: 789-798, Jan. 3, 2008.

Liu, et al., "HARP MRI Tagging for Direct Quantification of Lagrangian Strain in Rat Hearts After Myocardial Infarction" J. Biomech Eng., Aug. 2004; 126(4): 523-528.

Foster, et al., "Hybrid-III—a biomechanially-based crash test dummy (No. 770938)", S.A.E. Technical Paper, 1978.

APPARATUS FOR EXAMINING BRAIN INJURY, METHOD OF MAKING AND METHOD OF USING THE SAME

PRIORITY CLAIM AND CROSS-REFERENCE

This application is a continuation of U.S. application Ser. No. 16/256,308, filed Jan. 24, 2019, which claims the benefit of U.S. Provisional Application No. 62/621,854, filed Jan. 25, 2018, each of which applications is expressly incorporated by reference herein in its entirety.

FIELD OF THE INVENTION

The disclosure relates to study and detection of brain injury generally. More particularly, the disclosed subject matter relates to a test apparatus or system for measuring the effect of a head impact on a brain, a method of making and a method of using the test apparatus.

BACKGROUND

Chronic traumatic encephalopathy (CTE) is a progressive degenerative disease resulting from a head trauma and particularly a history of repetitive head trauma. Military personnel may be exposed to blasts and other head impacts, which may lead to development of CTE. Other environments where people may be subjected to head trauma include the health care industry, and industrial environments such as in a factory or construction site. Athletes participating in contact sports such as football, soccer, rugby and boxing incur repetitive head trauma that has been shown to lead to the development of CTE in some individuals. CTE may result from symptomatic concussions as well as sub-concussive head trauma. Many athletes may experience frequency sub-concussive head trauma during participation in a contact sport and never have a symptomatic concussion. These athletes may still develop CTE. The effect of these frequent head impacts is a growing concern.

CTE may result from repetitive damage to axons in the brain, such as shearing caused by high acceleration of the brain tissue. High acceleration is caused by rapid head velocity change, such as that caused by an impact to the head. Axons connect neurons in the brain. Damage to the axons can result in immediate effects and/or delayed effects, such as CTE. Brain injury, such as axonal shearing, may create neurochemical and neurometabolic cascade effects. Even mild trauma to the brain can result in neuronal depolarization, which leads to neuronal discharge and the release of neurotransmitters and increased extra cellular potassium ($K^+$). This may be followed by an increased glucose demand and metabolism (hyperglycolysis) and a resultant relative ischemia from reduced cerebral blood flow. Axonal injury may also result from an influx of extra cellular calcium that reduces cerebral blood flow through vasoconstriction, and the release of oxygen free radicals. These neurochemical and neurometabolic effects from even mild head trauma may result in the development of CTE.

SUMMARY OF THE INVENTION

The present disclosure provides a test apparatus or system for testing impact induced brain trauma or impairment, a method of making and a method using the same.

In accordance with some embodiments, the test apparatus or system comprises a head model. Such a head model comprises a skull component, a brain component, a fluid component. The skull component has a wall defining an interior chamber. The wall has an exterior wall surface and an interior wall surface. The brain component is disposed within the interior chamber, and comprises a gel material such as a polymeric gel or biological material for simulating brain tissues. The fluid component is disposed inside the interior chamber. In some embodiments, the system comprises a fluid tank, which is fluidly coupled with the skull component and is configured to provide the fluid component into the interior chamber.

In some embodiments, the skull component is made of a rigid and transparent material. The brain component may be in a spherical or any other suitable shape. In some embodiments, the brain component is shaped and sized to simulate a brain of a human subject.

In some embodiments, the fluid component has at least one portion disposed between the brain component and the interior wall surface of the skull component. The fluid tank is connected with the skull component through a tube. The fluid tank is configured to adjust a pressure of the fluid component inside the interior chamber in some embodiments.

In some embodiments, the head model further comprises a layer of porous media disposed between the brain component and the interior wall surface of the skull component. The layer of porous media comprises the fluid component disposed inside the porous media, and may be soaked with the fluid component.

In some embodiments, the system may include at least one impact element configured to provide an impact on the head model. The impact is translational or rotational or both. In some embodiments, the at least one impact element comprises a rotor coupled with the head model to provide a rotational impact on the head model.

The system may further comprise one or more sensors embedded inside or partially attached with the wall of the skull component. For example, the one or more sensors may be selected from the group consisting of a pressure sensor, a displacement sensor, an accelerometer, and a combination thereof. The system may also comprise a camera configured to take a plurality of images showing one or more components inside the interior chamber. The system may also include a computer and a computer program configured to analyze data from the one or more sensors and the plurality of the images for detecting impact induced brain trauma.

In another aspect, the present disclosure provides a method of forming the test apparatus or system as described herein. Such a method comprises forming a head model. The step of forming the head model comprises providing a skull component, having a wall defining an interior chamber, forming a brain component comprising a gel material for simulating brain tissues, placing the brain component within the interior chamber, and supplying a fluid component into the interior chamber from a fluid tank disposed outside the skull component. The fluid tank is fluidly coupled with the skull component so as to provide the fluid component into the interior chamber with a controlled pressure.

In some embodiments, the brain component is formed through steps including: three-dimensionally (3-D) printing a skull model based on anatomical data from computed topography (CT) scan of a head of a human subject, forming a negative casting mold based on the skull model, and casting the brain component inside the negative casting mold. In some embodiments, the data from a CT scan can be used to design a mold on a computer. The mold can be then made without 3D printing a skull model first.

In some embodiments, a layer of porous media may be placed between the brain component and the interior wall surface of the skull component. In some embodiments, at least one impact element may be also provided for giving an impact on the head model. The impact is translational or rotational or both.

In another aspect, the present disclosure provides a method of using a system for testing impact induced brain trauma as described herein. Such a method comprises a step of providing an impact on the head model from at least one impact element. The impact is translational or rotational or both. In the system, the head model may include a layer of porous media disposed between the brain component and the interior wall surface of the skull component. In some embodiments, a rotational impact on the head model is provided by a rotor in the at least one impact element. The rotor is coupled with the head model. In some embodiments, such a method includes steps of collecting data from one or more sensors embedded inside or partially attached with the wall of the skull component, taking a plurality of images through a camera to show one or more components inside the interior chamber, and analyzing the data and the plurality of images using a computer and a computer program so as to detecting impact induced brain trauma.

The present disclosure provides an approach to examine the flow and pressurization of the cerebrospinal fluid flow (CSF) in the subarachnoid space (SAS) as the head is imposed to sudden external impacts. The test apparatus or system includes an improved head model to better understand the mechanism of concussive and sub-concussive brain injuries, and to provide guidance for the prevention of such injuries. For example, the CSF flow through the soft, porous arachnoid trabeculae (AT) in the SAS, and both translational and rotational impact are considered. With consideration of the complicated nature of the biological system, a biomimetic approach is used to investigate the mechanism of brain injury.

BRIEF DESCRIPTION OF THE DRAWINGS

The present disclosure is best understood from the following detailed description when read in conjunction with the accompanying drawings. It is emphasized that, according to common practice, the various features of the drawings are not necessarily to scale. On the contrary, the dimensions of the various features are arbitrarily expanded or reduced for clarity. Like reference numerals denote like features throughout specification and drawings.

DETAILED DESCRIPTION

Figure 1A:
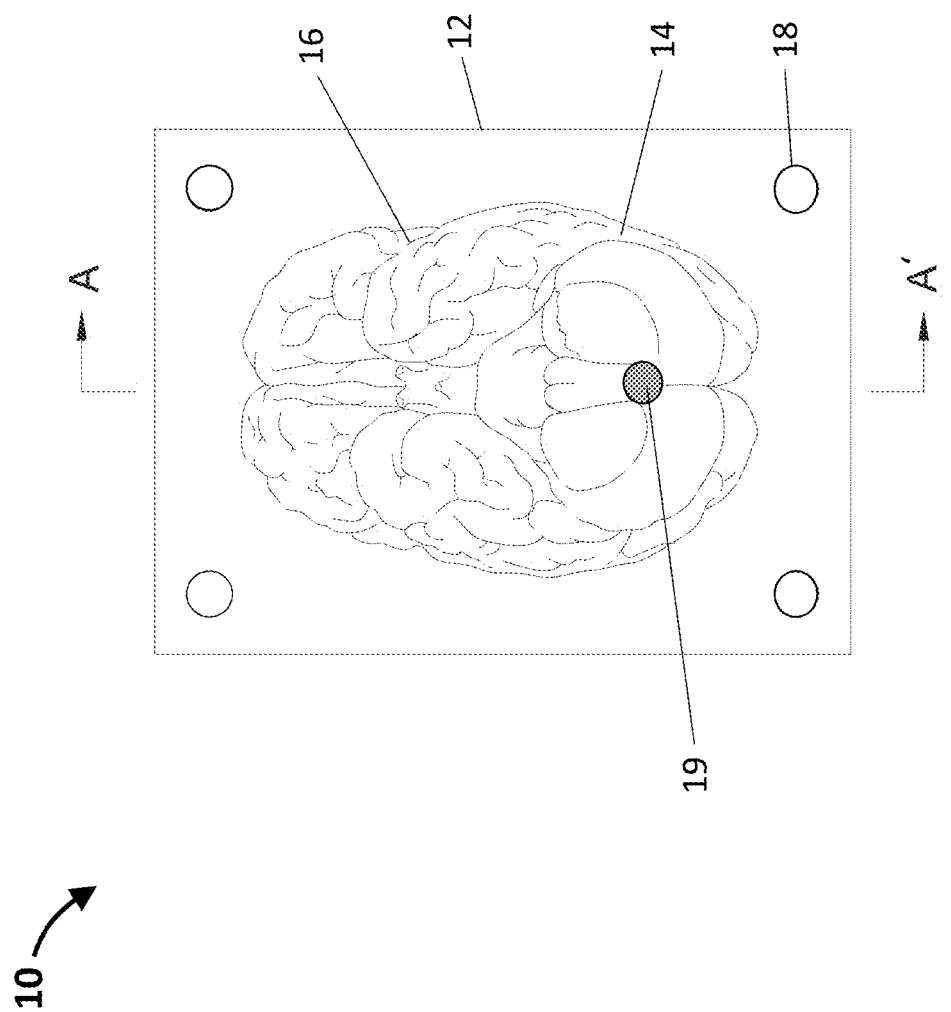
FIG. 1A is a plan view illustrating a first half (e.g., a bottom piece) of an exemplary mold for casting an artificial brain component in accordance with some embodiments.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

For purposes of the description hereinafter, it is to be understood that the embodiments described below may assume alternative variations and embodiments. It is also to be understood that the specific articles, compositions, and/or processes described herein are exemplary and should not be considered as limiting.

In the present disclosure the singular forms "a," "an," and "the" include the plural reference, and reference to a particular numerical value includes at least that particular value, unless the context clearly indicates otherwise. When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" preferably refers to a value of 7.2 to 8.8, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", "2-5", and the like. In addition, when a list of alternatives is positively provided, such listing can be interpreted to mean that any of the alternatives may be excluded, e.g., by a negative limitation in the claims. For example, when a range of "1 to 5" is recited, the recited range may be construed as including situations whereby any of 1, 2, 3, 4, or 5 are negatively excluded; thus, a recitation of "1 to 5" may be construed as "1 and 3-5, but not 2", or simply "wherein 2 is not included." It is intended that any component, element, attribute, or step that is positively recited herein may be explicitly excluded in the claims, whether such components, elements, attributes, or steps are listed as alternatives or whether they are recited in isolation.

The present disclosure provides a test apparatus or system for testing impact induced brain trauma or impairment, a method of making and a method of using the same. Each test apparatus or system has a respective head model, which includes at least a skull component and a brain component.

Unless expressly indicated otherwise, references to "a skull component" made herein will be understood to encompass a structure having a wall for forming an enclosure or interior cavity and including a material having density and mechanical strength close to or the same as those of a human skull. Such a material might be rigid. A skull component may be in a spherical or any other shape. In some embodiments, it is shaped and sized to simulate or mimic a skull of a human subject.

Unless expressly indicated otherwise, references to "a brain component" made herein will be understood to encompass a structure made of a soft material having density and mechanical strength close to those of a human brain. A brain component may be in a spherical or any other shape. In some embodiments, it is shaped and sized to simulate or mimic a brain of a human subject.

Unless expressly indicated otherwise, references to "a fluid component" made herein will be understood to encompass a fluid or a solution, which might be aqueous. Such a fluid may have a density or a composition similar to that of cerebrospinal fluid. In some embodiments, water or a saline solution is used.

Unless expressly indicated otherwise, references to "an impact element" made herein will be understood to encompass a structure configured to provide an impact onto a head model. An impact element may be configured to simulate any number of different types of impact surfaces and orientations. In some embodiments, such an impact is translational, rotational, or both.

An impact element may be configured to simulate any number of different types of impact surfaces and orientations. For example, an impact element may include or simulate concrete, the ground, metal, a bat, a ball, a vehicle, a person's head (e.g., to simulate a head impact during a soccer game), or other impact element. The impact element can be precisely controlled by an actuator to provide consistent impacts on the simulated head model, the consistent impacts having consistent physical parameters, including but not limited to impact velocity and/or acceleration. The actuator may be controlled to move the impact element at any suitable velocity and/or acceleration throughout the stroke or travel distance of the impact element. As described herein, the impact element may be controlled to retract back quickly after providing the impact directly or indirectly to the head model. An impact simulator may comprise one, two or more impact elements configured to impact the head model at substantially the same time, or in rapid succession, for example, or at different locations.

Figure 14:
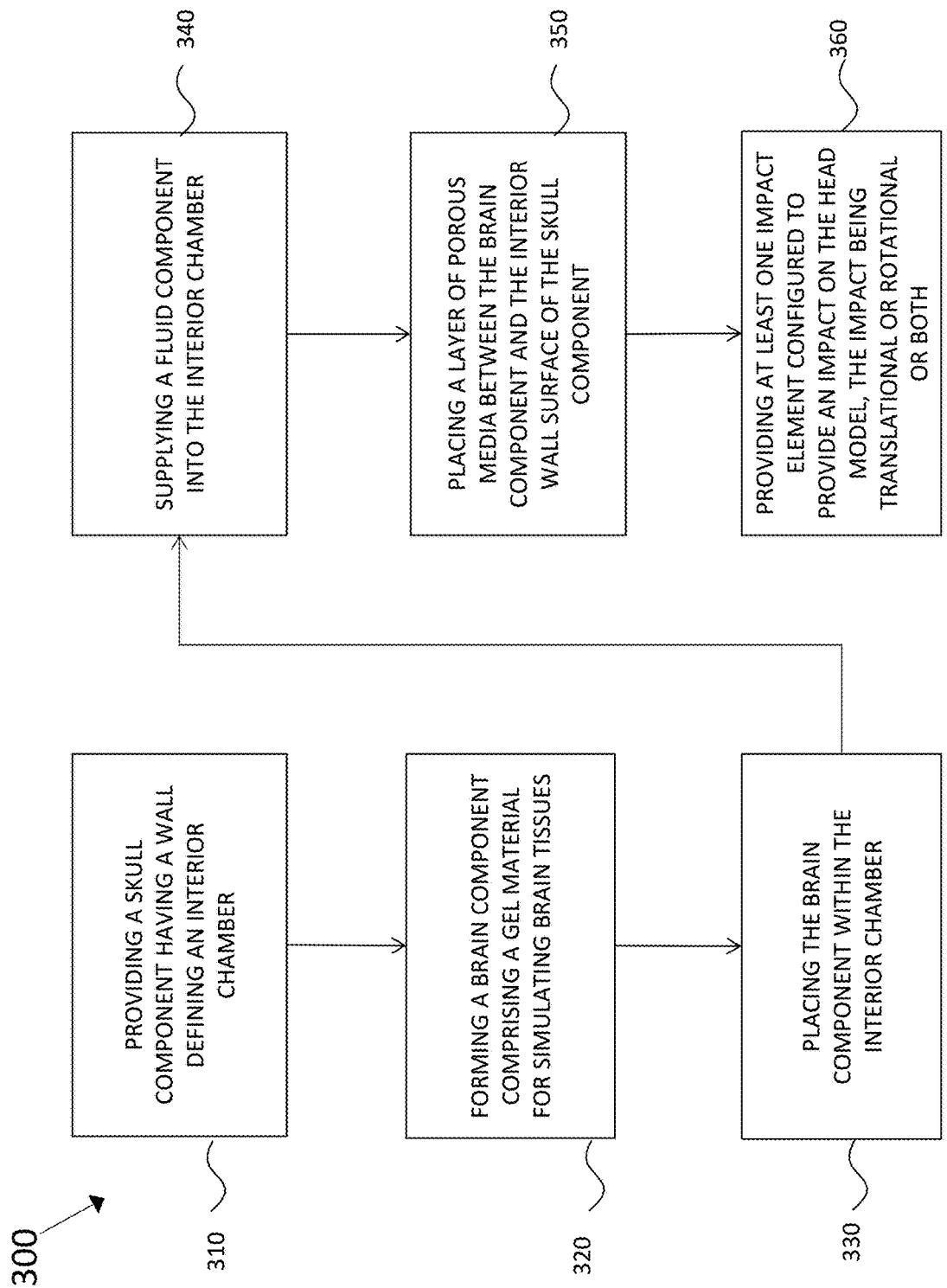
FIG. 14 is a flow chart illustrating an exemplary method of making an exemplary system in accordance with some embodiments.
Figure 15:
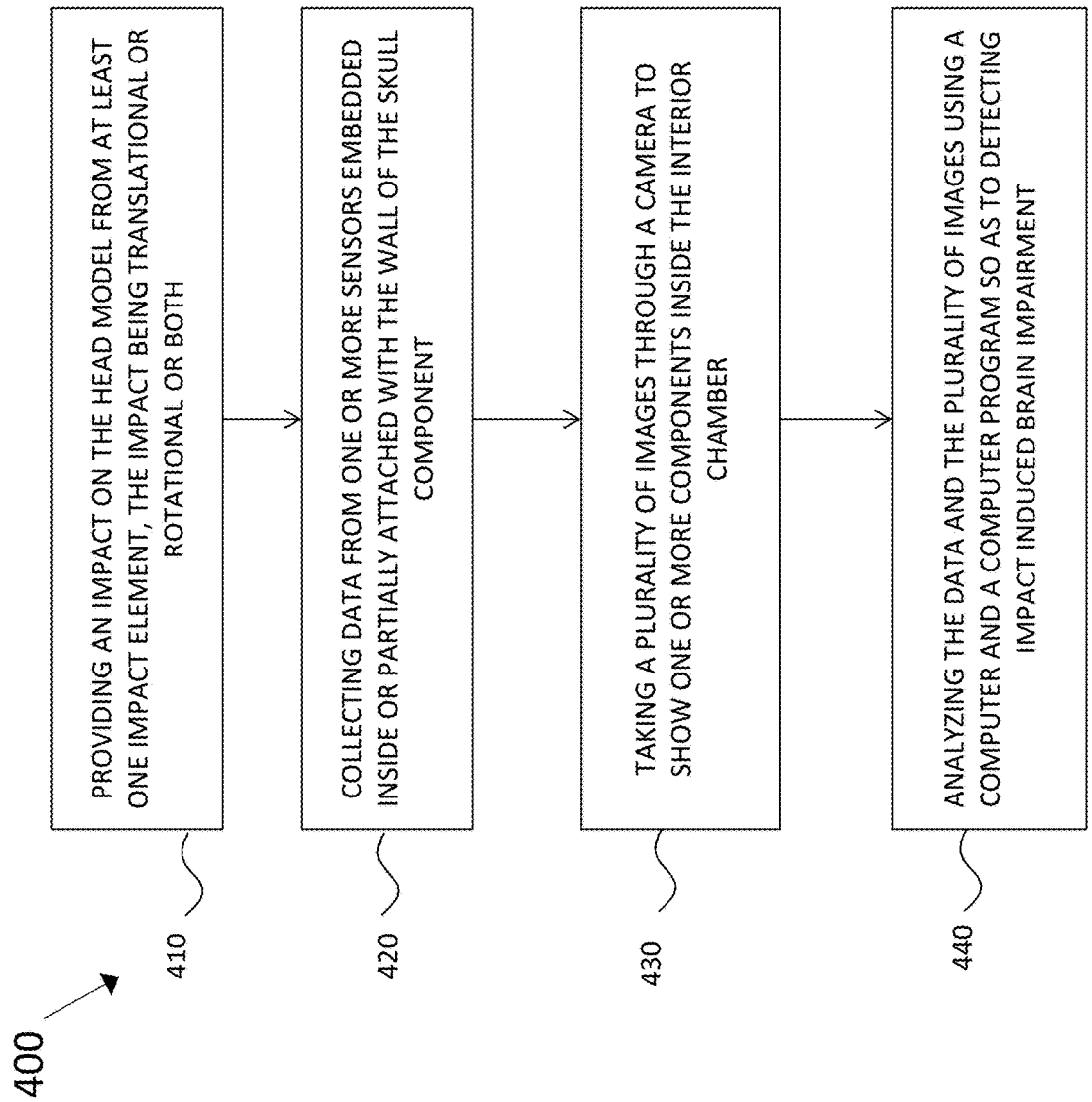
FIG. 15 is a flow chart illustrating an exemplary method of using an exemplary system in accordance with some embodiments.

In the drawings, like items are indicated by like reference numerals, and for brevity, descriptions of the structure, provided above with reference to the preceding figures, are not repeated. The method described in FIG. 4 are described with reference to the exemplary structure described in FIGS. 1-3. FIGS. 6-13 describes in detail the test apparatus or systems having a respective head model illustrated in the scheme of FIG. 5. In each model, other components may not be shown. For example, one or more head exterior components for simulating hair and skin may extend around the perimeter of each skull component. FIG. 14 illustrates an exemplary method of making a system comprising each head model as described in FIGS. 6-13. FIG. 15 illustrates an exemplary method of using a system comprising each head model as described in FIGS. 6-13.

1. Brain Component:

FIGS. 1A-1B, 2A-2B, 3 and 4 describe an exemplary mold and an exemplary method for forming a brain component.

Figure 1B:
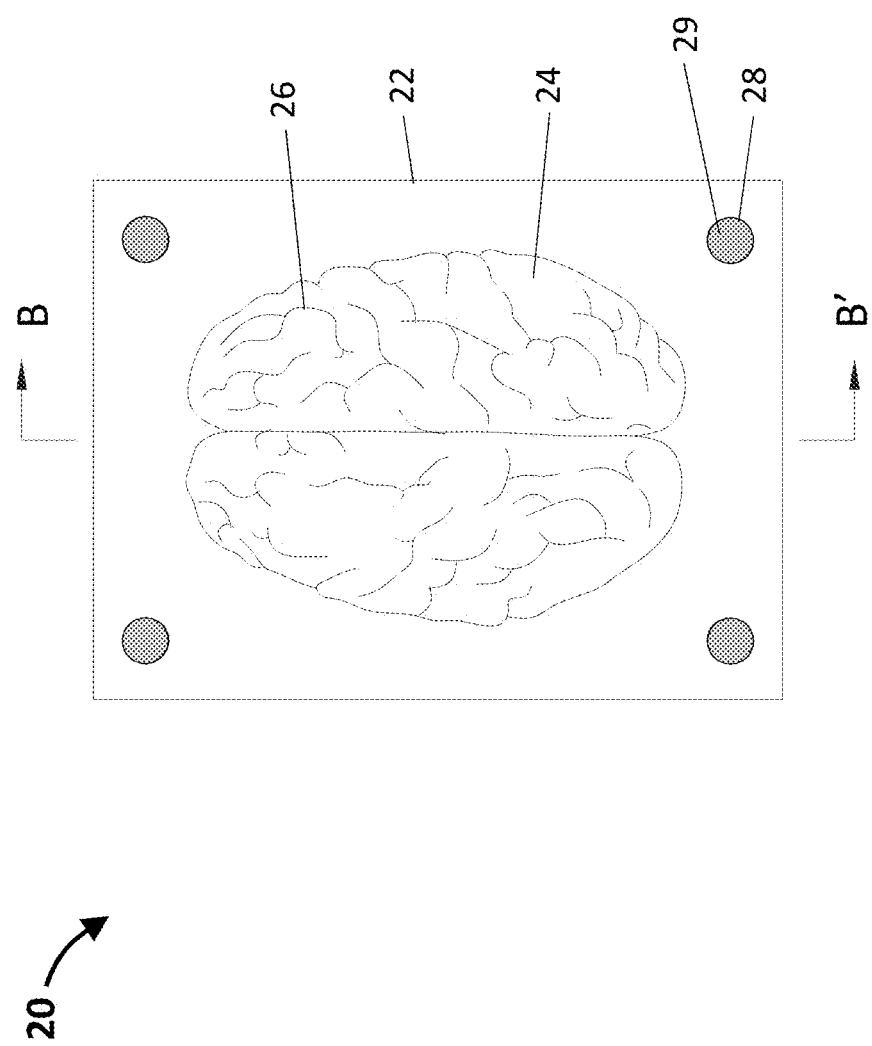
FIG. 1B is a plan view illustrating a second half (e.g., a top piece) of an exemplary mold for casting an artificial brain component in accordance with some embodiments.
Figure 2A:
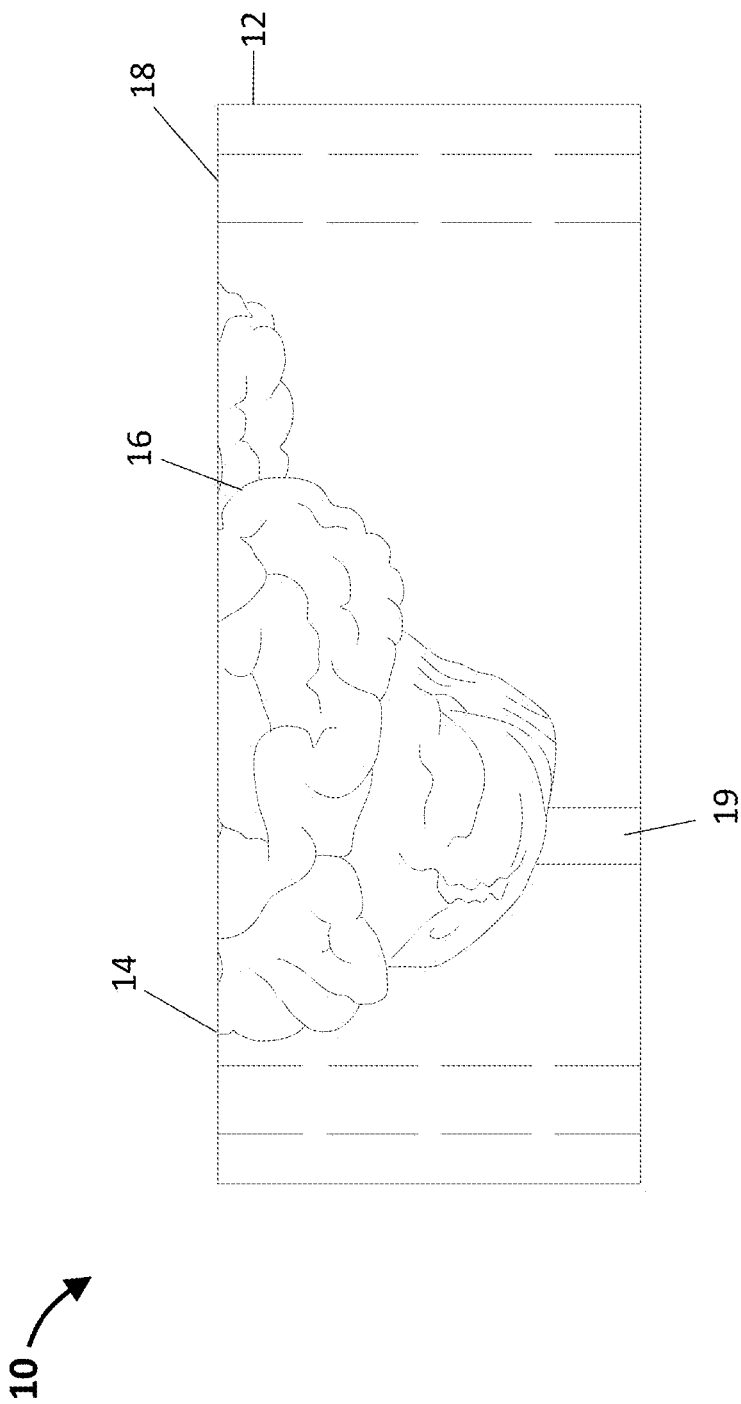
FIG. 2A is a sectional view illustrating the first half of the exemplary mold as shown in FIG. 1A.
Figure 2B:
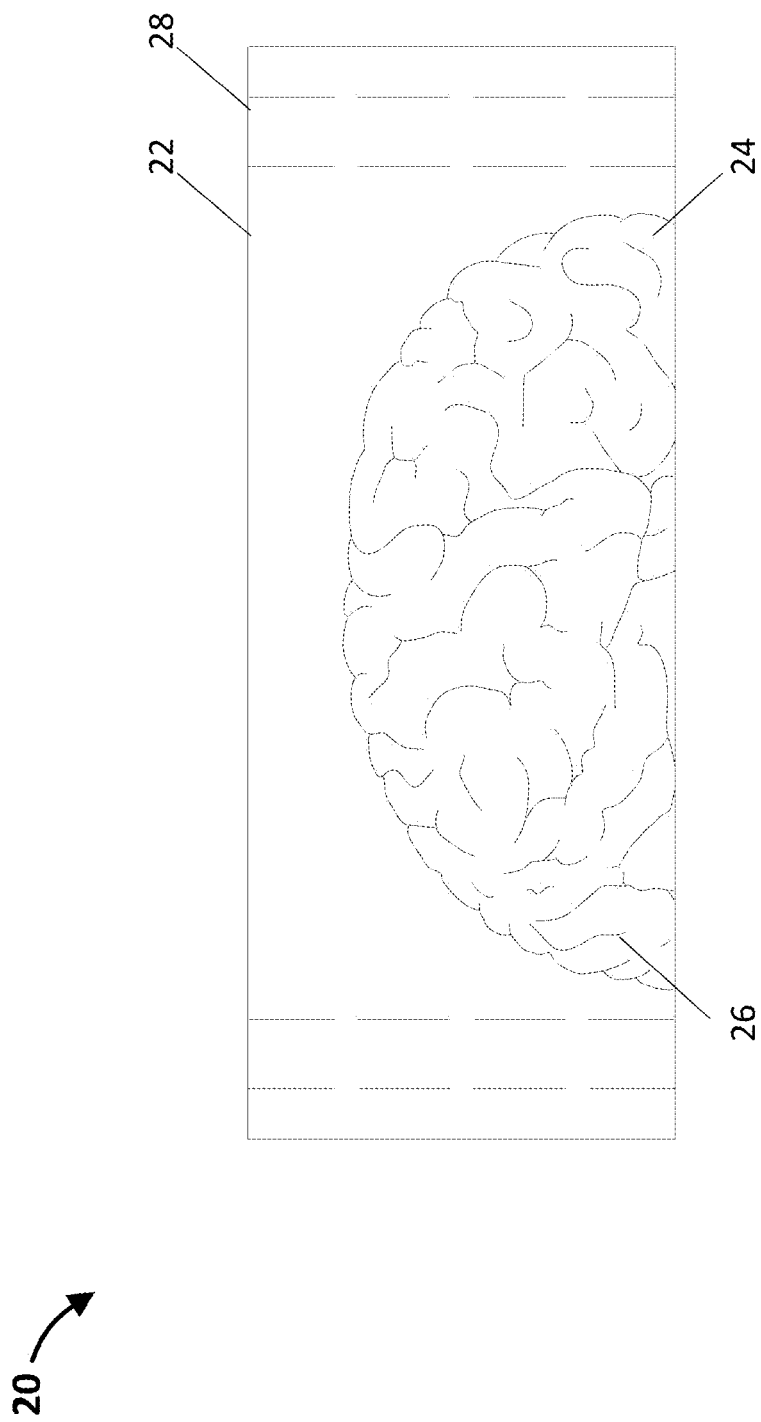
FIG. 2B is a sectional view illustrating the second half of the exemplary mold as shown in FIG. 1B.

Referring to FIGS. 1A-1B and 2A-2B, an exemplary mold includes a first half of mold 10 such as a bottom mold piece and a second half of mold 20 such as a top mold piece. FIGS. 1A and 2A are plan views while FIGS. 1B and 2B are sectional views along lines A-A' and B-B', respectively. Such a mold is used for forming an artificial brain matter or a brain component 30. The two halves of mold 10, 20 may be made of a metal or a polymer such as a thermoset acrylic polymer, or any other suitable material.

Referring to FIGS. 1A and 2A, the first half of mold 10 includes a first mold plate 12 defining a first mold cavity 14, which may have surface features 16 reflecting and simulating surface morphology of a brain of a human subject. The first half of mold 10 may also define holes 18 for bolts in each corner, and may be so configured that a support 19 for a brain component can be inserted into the first mold cavity 14 during a molding process.

Referring to FIGS. 1B and 2B, the second half of mold 20 includes a second mold plate 22 defining a second mold cavity 24, which may have surface features 26 reflecting and simulating surface morphology of a brain of a human subject. The second half of mold 20 may also define holes 28 for bolts 29 in each corner. The bolts 29 can be inserted into the holes 18 of the first half of mold 10 when the two halves of mold 10, 20 are assembled together during a molding process.

Figure 3:
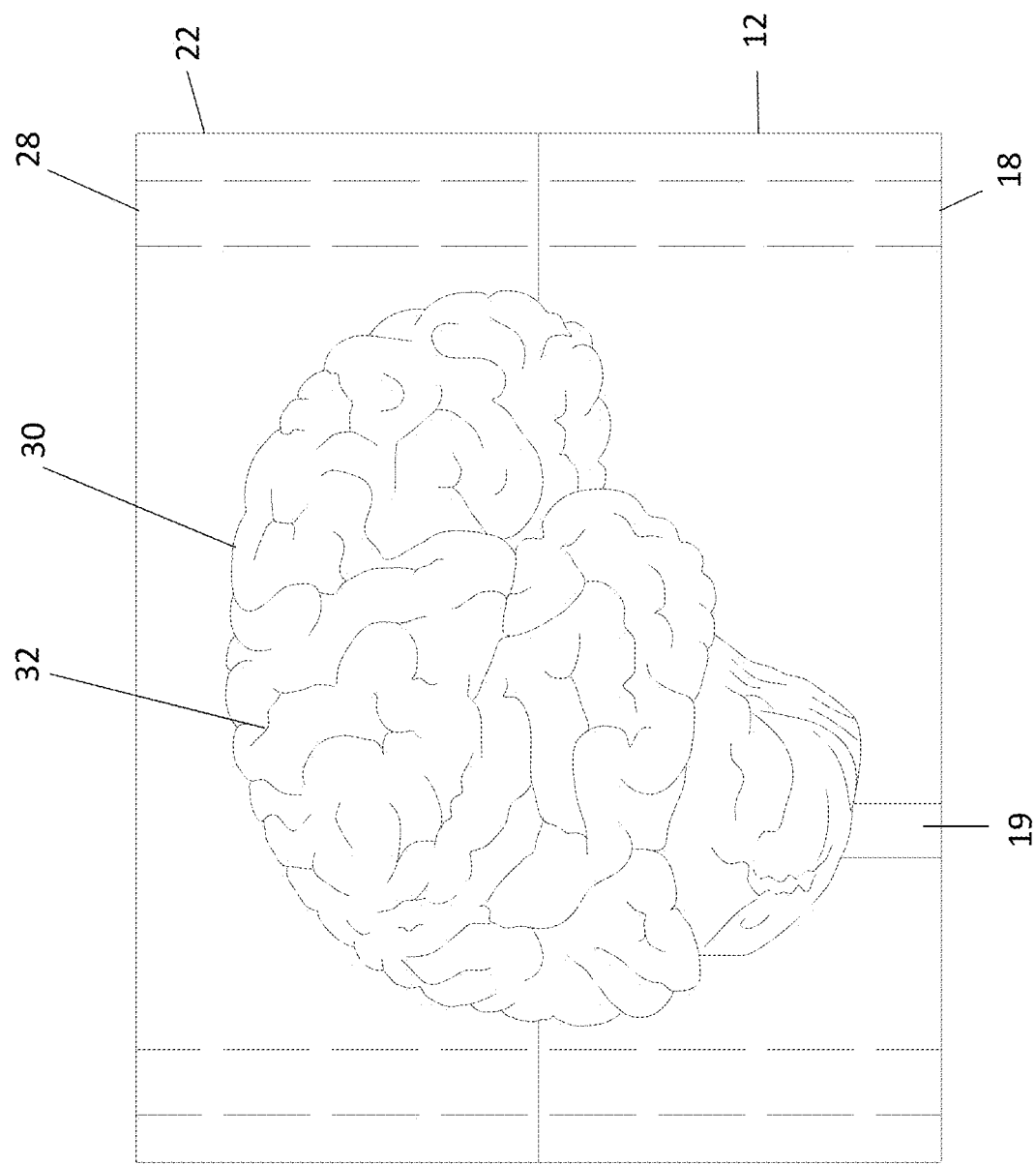
FIG. 3 is a sectional view illustrating the exemplary mold when the first half as shown in FIG. 2A and the second half as shown in FIG. 2B are closed in accordance with some embodiments.
Figure 4:
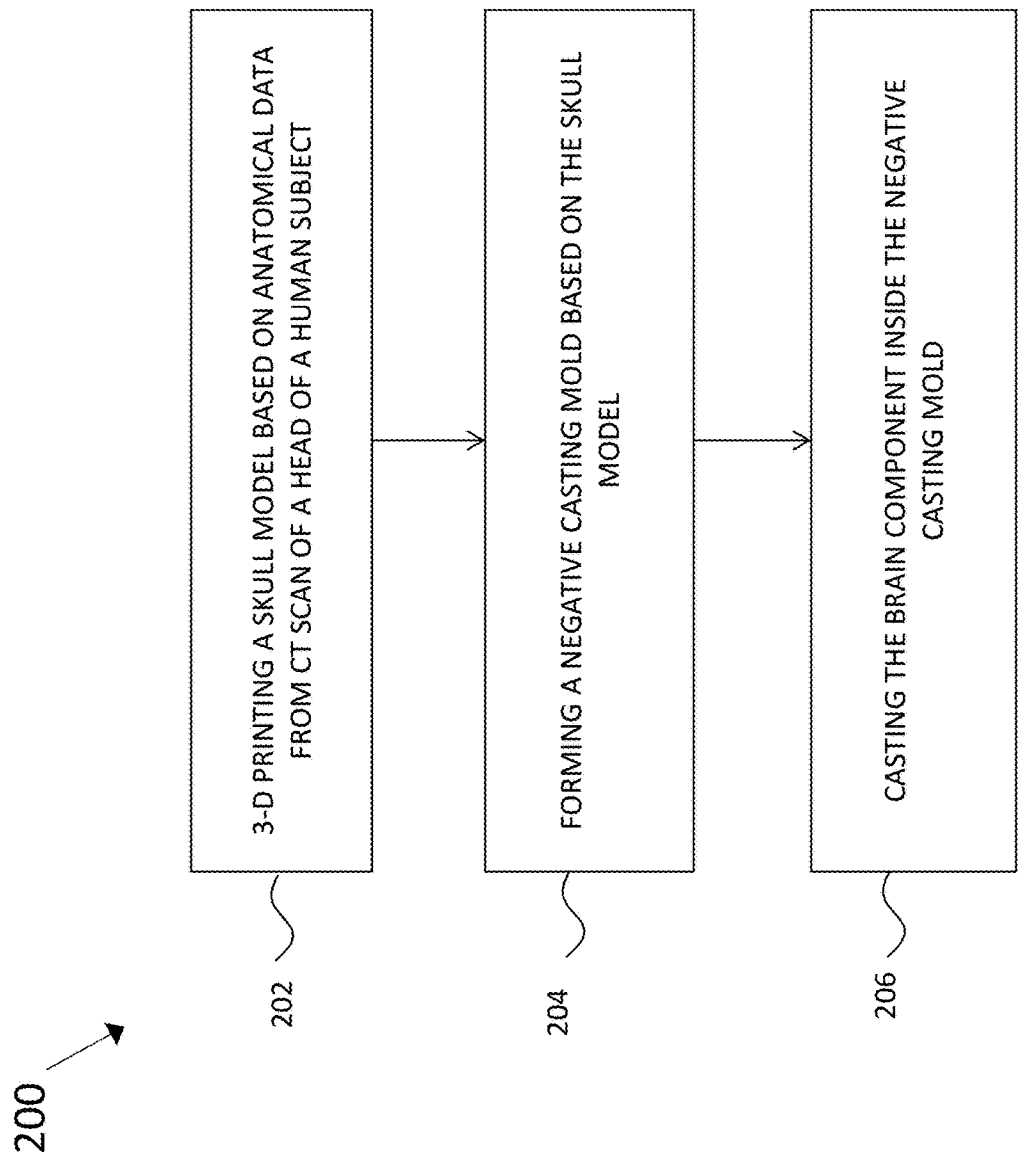
FIG. 4 is a flow chart illustrates an exemplary method for casting an artificial brain component in accordance with some embodiments.

Referring to FIG. 3, when the two halves of mold 10, 20 are assembled together, a brain component 30 can be molded or casted by using a suitable material fed into the mold cavity. In some embodiments, the brain component 30 may have a spherical shape. In some embodiments, the brain component 30 may have a size, a shape, and surface features 32 simulating a brain of a human subject. The brain component 30 may comprise a gel material such as a polymeric gel or biological material for simulating brain tissues.

Referring to FIG. 4, an exemplary method 200 is described for forming a brain component 30 in accordance with some embodiments. At step 202, a skull model may be made through three-dimensional (3-D) printing based on anatomical data from computed topography (CT) scan of a head of a human subject. At step 204, a negative casting mold is made based on the skull model. Such a mold may include two mold pieces 12, 22 (i.e. two halves) as described above. In some embodiments, the data from a CT scan can be used to design a mold on a computer. The mold can be then made without the step of 3D printing a skull model first. In some embodiments, the mold has a size of a human brain based on a brain anatomical model. The mold may be made of a thermoset acrylic polymer in some embodiments.

At step 206, the brain component 30 is casted or molded inside the negative casting mold. In some embodiments, the material for the brain component 30 is a polymeric gel such as a silicone gel. The silicone gel may be crosslinkable through a platinum-catalyzed curing system, and may have a shore 00 hardness in a range of from 10 to 50. Such silicone gel materials is available under trademark ECO-FLEX® from Smooth-On Company in Pennsylvania, USA. For example, two types of silicone gel materials ECO-FLEX® 00-30 (having shore 00 hardness of 30) and ECO-FLEX® 00-20 (having shore 00 hardness of 20) were used. Each of these two silicone gel materials was poured into the mold (FIG. 3) to cast a brain component 30.

In the step 206, the following procedures were followed in some experimental trials. A silicone material and a catalyst are mixed. A mold release is sprayed onto the internal surfaces of the mold pieces 12, 22. The support 19 to the brain component 30 such as a neck component, which is a solid structure, is put into the mold. The mold pieces 12, 22 are assembled together. In some embodiments, any possible gap between can be sealed by using clay. After fully mixed, the silicone material is degassed in a vacuum box to avoid formation of cavities in the resulting brain component 30. The silicone material is poured into the mold through a feeding port. Vacuum is applied to extract air possibly trapped in the mold while the mold is shaken slightly. The silicone material is cured overnight in the mold. A brain component 30 made of silicone gel is removed from the mold.

Tensile tests were performed to examine tensile properties of the silicone gel materials including ECOFLEX® 00-30 and ECOFLEX® 00-20. Flat silicone gel sheets were obtained by casting in a flat mold. The dimensions of the sheets were 15.2 cm×26 cm×0.2 cm. Due to high flexibility of the materials, it is not feasible to prepare an ideal dog-bone shaped tensile specimen using machining methods. Therefore, a steel hole-punch (7.9 mm in diameter) was used to prepare quasi-dog-bone specimens. An MTS BIONIX® universal testing machine with a load cell of 100 N were used to conduct the tensile tests. The crosshead speed of the MTS machine was set at 10 mm per second. Strain gages could not be attached to the specimens, so an alternative approach was used to estimate the strain reading. For all the tests, the initial distance between the upper and lower grips was kept at 11 mm, and was adopted as the original gage length to calculate the strains for all the tensile specimens. The measured maximum tensile strength of silicone sheets made of ECOFLEX® 00-30 and ECOFLEX® 00-20 was about 0.9 MPa and 0.66 MPa, respectively. The measured Young's modulus of silicone sheets made of ECOFLEX® 00-30 and ECOFLEX® 00-20 was about 0.13 MPa and 0.068 MPa, respectively.

Soft silicone gel materials are described for illustration purpose. Any other suitable materials may be used to cast or mold a brain surrogate.

2. Head Models and Resulting System:

In the present disclosure, a novel approach is proposed to examine the flow and pressurization of the cerebrospinal fluid flow (CSF) in the subarachnoid space (SAS) when the head is exposed to sudden external impacts. The goal is to better understand the mechanism of concussive and sub-concussive brain injuries, and to provide guidance for the prevention of such injuries. The brain can be treated as a soft tissue bathed in the fluid (i.e. CSF), which is enclosed by a rigid structure, i.e., a skull. The brain concussion is a type of brain injury within an intact skull. The concussive and sub-concussive injuries occur as a result of a series of fluid-structure-interactions (FSI) between the rigid skull, the CSF and the soft brain matter. The deformation of the brain is a main reason for the brain concussion. The strain of the brain tissue needs to be used as an indicator for the brain injury. The impact duration is very short and thus the FSI is extremely transient. The CSF flow through the soft, porous arachnoid trabeculae (AT) in the subarachnoid space (SAS) plays a crucial role in this process. Considering the complicated nature of the biological system, a biomimetic approach is proposed herein to investigate the mechanism of brain injury.

The present disclosure provides a test apparatus or system including a head model 50. The head model 50 includes a brain component 30, a skull component 82, and a fluid component 84. In some embodiments, the head model 50 further includes a layer of porous media 102 disposed between the brain component 30 and the skull component 82. Such a system may include at least one impact element 70 configured to provide an impact on the head model. The impact is translational or rotational or both.

Figure 5:
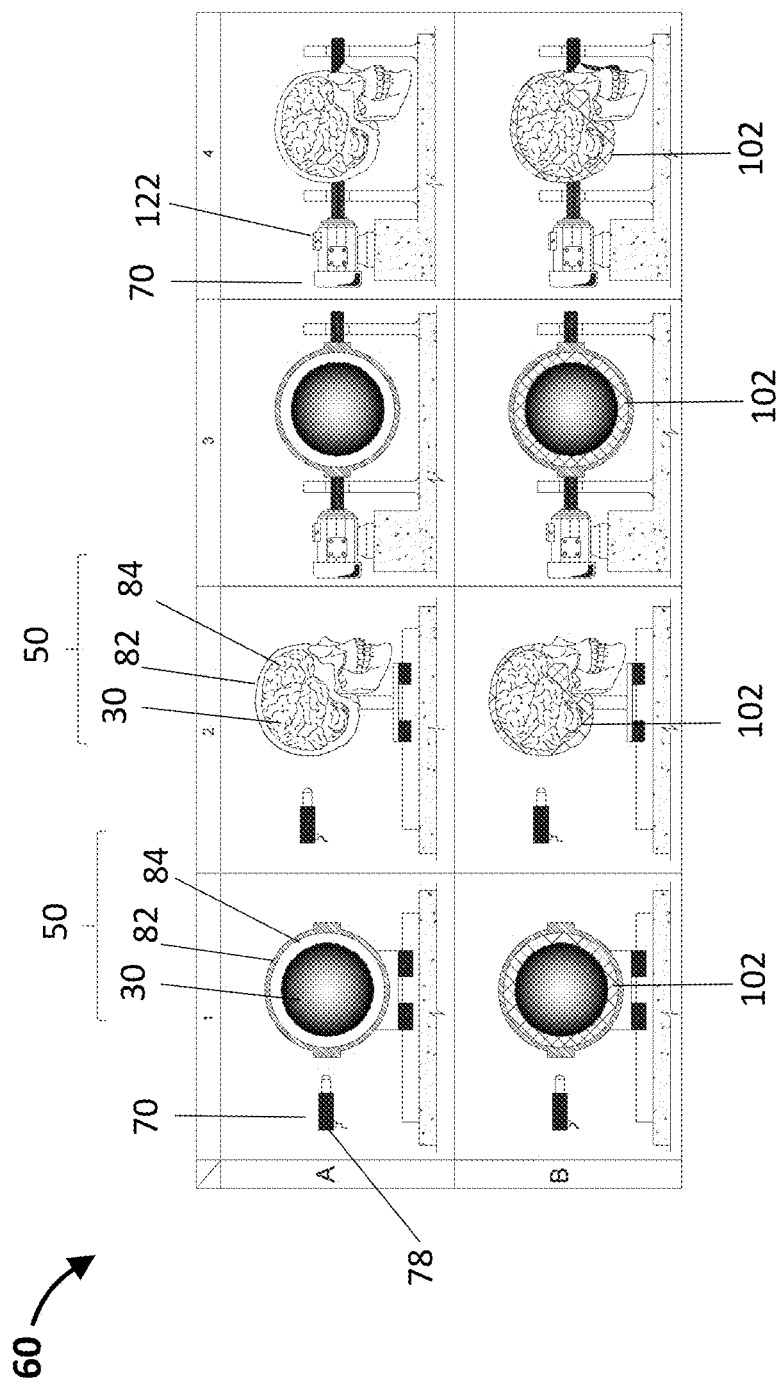
FIG. 5 is a schema illustrating different test apparatus for testing translational and rotational impacts of head on brains in accordance with some embodiments. Each test apparatus is illustrated in more details in one respective figure of FIGS. 6-13, which are sectional views.

FIG. 5 illustrates different head models and the resulting systems, which are described in detail in FIGS. 6-13. Two types of impacts are considered, translational and rotational. The at least one impact element 70 may include a linear impactor 78 to provide translation impact, and/or a rotor 122 to provide rotational impact. As shown in Sections 1A, 1B, 2A, and 2B in the chart of FIG. 5, a linear impactor 78 may be used. As shown in Sections 3A, 3B, 4A, and 4B in the chart of FIG. 5, a rotor 122 may be used. Two types of experimental setups are considered, including a spherical apparatus (illustrated in Sections 1A-1B and 3A-3B of FIG. 5), and a simulated head surrogate (illustrated in Sections 2A-2B and 4A-4B of FIG. 5). Both have the testing material bathed in a liquid environment. Various soft materials are considered to simulate the soft brain matter, from artificial gel type of soft materials to a real porcine brain. The artificial gel like materials may be coated with porous media 102 (as illustrated in Sections 1B, 2B, 3B and 4B of FIG. 5) for studying the role of arachnoid trabeculae (AT) in transmitting impact on a head.

Figure 6:
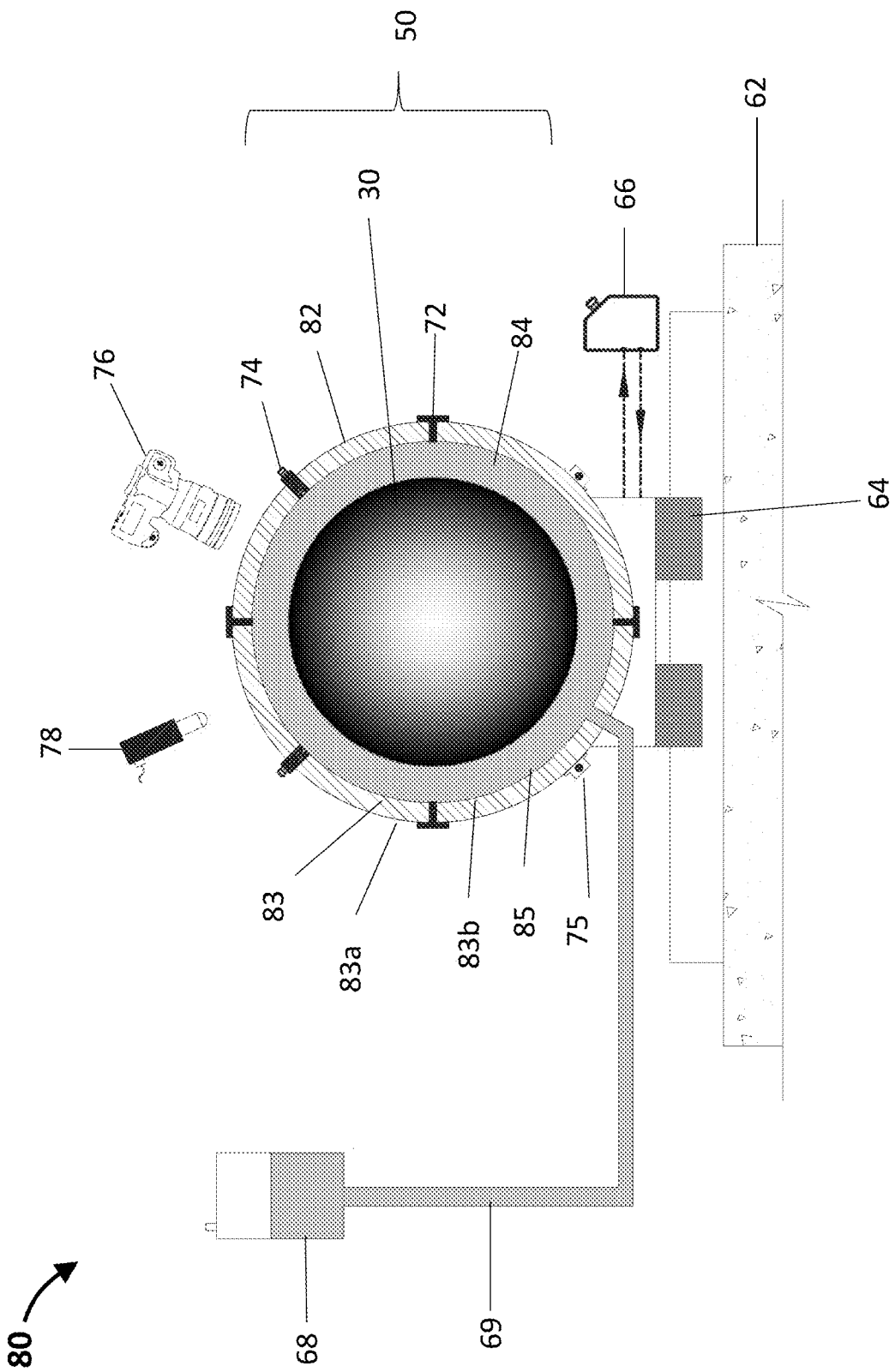
FIG. 6 illustrates an exemplary apparatus including artificial brain in a shape of an inner sphere for testing translational impact in accordance with some embodiments.

Referring to FIG. 6, an exemplary apparatus 80 is used in some embodiments.

The exemplary apparatus 80 includes an artificial brain component 30 in a spherical shape in a head model 50. The spherical shape is for illustration only. The brain component 30 may be in any other suitable shape.

The head model 50 is disposed on a support 62 with a slider 62 or other accessory fixtures. The slider 62 is used to support the skull component 82 in the head model 50 and allow the skull component 82 to move linearly.

The skull component 82 has a wall 83 defining an interior chamber or cavity 85. The wall 83 has an exterior wall surface 83*a* and an interior wall surface 83*b*. In some embodiments, the skull component 82 is made of a rigid and transparent material. The brain component 30 is disposed within the interior chamber 85, and includes a gel material such as a polymeric gel or biological material for simulating brain tissues.

The brain component 30 can be made of various materials including, but not limited, to casted artificial brain matter (e.g., silicone gel), a porcine brain, and a brain component made of chicken eggs. The mechanical behavior (e.g., stiffness) of a porcine brain as well as the artificial brain matter can be characterized using an atomic force microscope (AFM). Considering the density and other properties of the brain vary with age, gender and many other reasons, the choice of materials for the brain component 30 provides a full spectrum to examine the influence from different impact processes.

The fluid component 84 is disposed inside the interior chamber 85. In some embodiments, the system includes a fluid tank 68, which is fluidly coupled with the skull component 82 through a tube 69 and is configured to provide the fluid component 84 into the interior chamber 85. In some embodiments, the fluid component 84 has at least one portion disposed between the brain component 30 and the interior wall surface 83b of the skull component 82. A gap exists between the brain component 30 and the skull component 82 in some embodiments.

Different types of fluid can be filled into the tank 68 to simulate the CSF. The density and other properties of CSF vary with age, gender and many other reasons. The choice of liquid for the fluid component 84 provides a full spectrum to examine the influence from an impact process. The fluid tank 68 may be configured to adjust a pressure of the fluid component 84 inside the interior chamber 85 in some embodiments. In some embodiments, the pressure of the fluid component 84 may be controlled via a U-tube type setup with the liquid tank 68. The ambient pressure inside the tank 68 and the height of the tank 68 can be varied leading to different liquid pressures inside the container.

The system or apparatus 80 may include a linear impactor 78 to provide translational impact on the head model 50. The linear impactor 78 is configured to create a sudden translational impact on the skull component 82, which is further transmitted to the brain component 30 via the fluid gap of the fluid component 84 between the brain component 30 and the skull component 82.

The system or apparatus 80 may further include one or more sensors embedded inside or partially attached with the wall 83 of the skull component 82. For example, the one or more sensors may be selected from a pressure sensor 72, a displacement sensor 74, an accelerometer 75, and a combination thereof. A laser sensor 66 may be also used to monitor the movement of the head model 50. The experimental setup uses instrumented sensors to measure the motion, velocity and the acceleration of the skull component 82, the pressure distribution of fluid, as well as the motion and deformation of the brain component 30 (FIG. 6).

The system or apparatus 80 may also include a high-speed camera 76 configured to take a plurality of images showing one or more components inside the interior chamber 85 The outer shell of the skull component 82 is transparent to allow direct visualization of the motion of the inner sphere using such the high-speed camera 76. The motion and deformation of the brain component 30 will also be captured by a high-speed camera.

The system may also include a computer (not shown) with a computer program configured to analyze data from the one or more sensors and the plurality of the images for detecting impact induced brain trauma or impairment.

Figure 7:
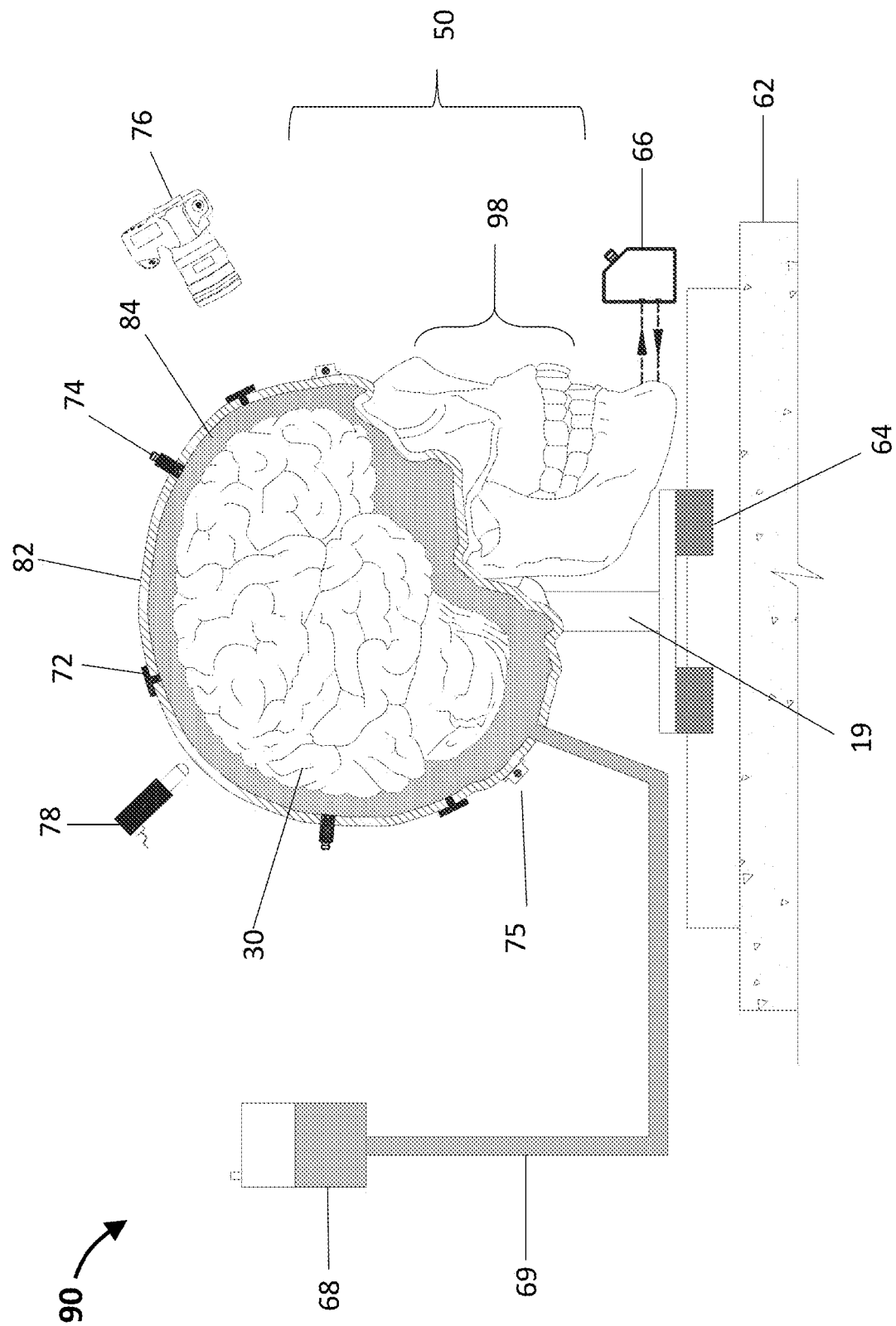
FIG. 7 illustrates an exemplary apparatus including head surrogate for testing translational impact in accordance with some embodiments.

Referring to FIG. 7, an exemplary apparatus 90 is used in some embodiments. The exemplary apparatus 90 is the same as the exemplary apparatus 80 except the shape of the head model 50 (i.e., a head surrogate) and related neck support. The components having the same reference numerals are described in FIG. 6. The exemplary apparatus 90 includes a head model 50 and an artificial brain component 30 simulating those of a human subject. The head model 50 and the brain component can be patient-specific. Similar to the exemplary apparatus 80, the exemplary apparatus 90 is also used for testing translational impact in accordance with some embodiments.

A biomimetic approach is used to model the human brain. The system includes a skull component 84, a molded brain component 30, supporting structure, and the intracranial fluid, as shown in FIG. 7. As described in FIGS. 1-4, precise anatomical data from a CT scan is used to 3-D print a skull component 82 and form the negative casting mold for the brain component 30. The skull component is transparent to allow inspection of the motion and deformation of the brain matter using a high-speed camera. The artificial brain-like material such as silicone gel is used to perform the test, and is casted by the negative brain mold using the casting approach as described in FIGS. 1-4. In some embodiments, a porcine brain can be tested as well. Due to its soft nature, instead of using electrical sensors, the motion of the real brain can be measured by a high speed camera.

As illustrated in FIG. 7, a support 19, such as an artificial hybrid neck used in dummy crash testing, is used to support the head model 50 including the casted brain component 30 and the skull component 82. The head model 50 may be coupled to a mount to restrain and provide stability during an impact test. In some embodiments, a neck spring may couple the head model 50 to a mount and may be flexible to enable some deflection and movement of the head model 50 during an impact test. A neck spring may be made out of a flexible material that can be physically returned to an original position. A neck spring may include one or more springs. The impact element 78 may be configured to impact the head model and then quickly retract, thereby allowing the head model 50 to spring back or recoil from the impact. This simulates real world impacts or accelerations, such as a rear-end car accident.

The skull component 82 is instrumented with an accelerometer 75 to measure its velocity and acceleration. Displacement sensor 66 mounted on a frame measures the motion of the skull component 82 due to impacts. Displacement sensor 74 mounted on the skull will measure the instantaneous variation of the subarachnoid space (SAS) due to the motion of the brain matter 30 relative to the skull component 82. A gyroscope placed at the location of the medulla oblongata provides data for the angular velocity of the head surrogate. Multiple pressure sensors 72 mounted on the skull or inside the skull capture the simulated pressure response of the CSF inside the SAS.

Figure 8:
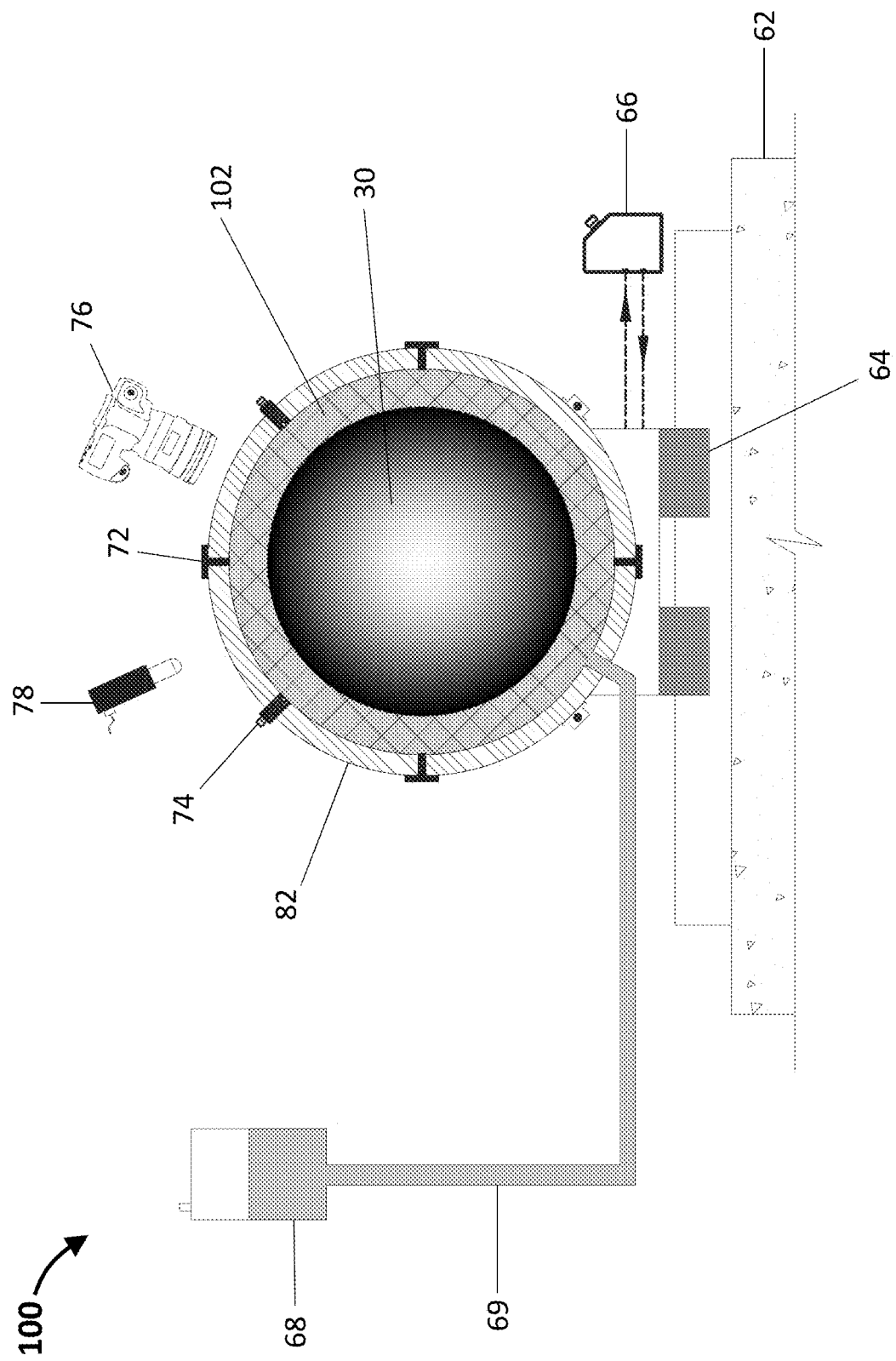
FIG. 8 illustrates an exemplary apparatus including artificial brain in a shape of an inner sphere and porous media for testing translational impact in accordance with some embodiments.

Referring to FIG. 8, an exemplary apparatus 100 is illustrated. The exemplary apparatus 100 is the same as the exemplary apparatus 80 except that the exemplary apparatus 100 includes a layer of porous media 102 for simulating porous arachnoid trabeculae (AT). In some embodiments, the head model 50 further includes a layer of porous media 102 disposed between the brain component 30 and the interior wall surface of the skull component 82. The layer of porous media 102 includes the fluid component 84 disposed inside the porous media 102, and may be soaked with the fluid component 84. In some embodiments, the layer of porous media 102 is made any suitable material having damping properties. In some embodiments, the layer of porous media 102 is made of a supermolecular polymer having a net or net-like structure. Such a polymer may be electrospun.

In order to examine the effect of the porous media, the skull component 82 is filled with a soft fibrous porous structure with variable permeability (i.e., the layer 102). Various functionalized supramolecular porous layers (SML) are prepared using an electrospinning process. An electrospinning system includes a power supply, a syringe array and syringe pump, two rollers and a controller. Solutions of polymers such as poly (vinylidene fluoride), poly (vinylidene fluoride-co-hexafluoro-propylene), polyvinyl pyrrolidine, polylactic acid polyacrylonitrile, poly (ethylene glycol), or any other polymers can be sprayed on a conveyer belt. The speed and spray frequency are controlled to provide SML with various pore size, stiffness, and thickness. The fiber diameter and/or thickness of the SML can be tailored and characterized by scanning electronic microscopy (SEM). The SML as the layer of porous media 102 can be disposed in the skull component 82 to allow for examination of the transient flow behavior in an enclosed skull component 82 filled with porous media 102.

Figure 9:
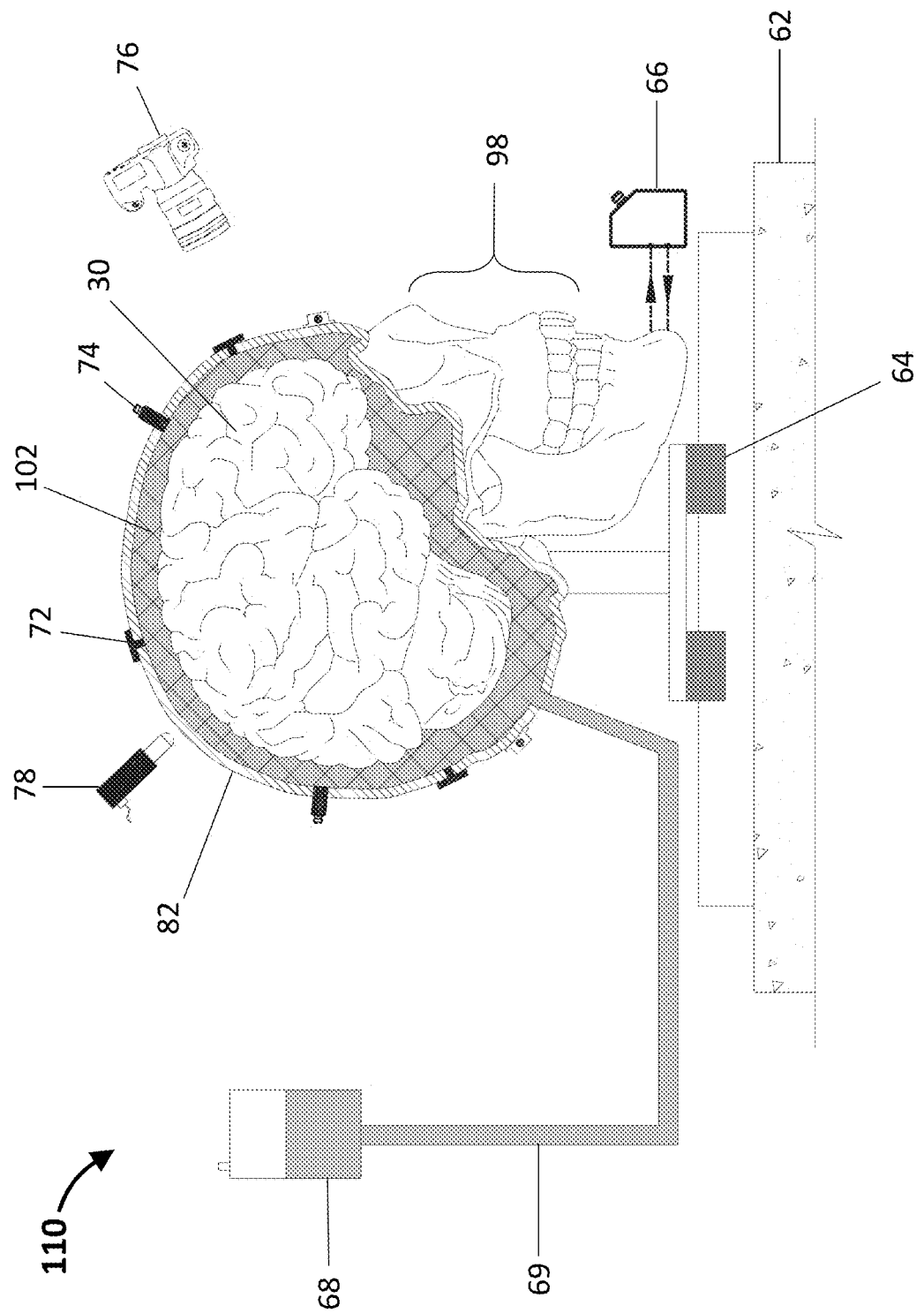
FIG. 9 illustrates an exemplary apparatus including head surrogate having porous media for testing translational impact in accordance with some embodiments.

Referring to FIG. 9, an exemplary apparatus 110 is illustrated. The exemplary apparatus 110 is the same as the exemplary apparatus 90 except that the exemplary apparatus 100 includes a layer of porous media 102 as described in FIG. 8. In some embodiments, the brain matter or component 30 is coated with functionalized porous SML to simulate the porous arachnoid trabeculae (AT). Comparisons of the response of the brain matter to the same external impacts can be made between SML coated and no-SML coated brain models. The porosity, permeability and fiber stiffness of the SML can be varied, and the effect of disturbance can be evaluated in the structure of the AT in the case of concussive or sub-concussive brain injury.

Parametric studies can be performed to examine the response of the same brain component 30 to different impact conditions, or the response of different brain components 30 to the same impact condition. The variations of the parameters include, the mechanical properties of the skull component 82 and the brain component 30, and the mechanical and transport properties of the SML.

FIGS. 10-13 illustrate four exemplary apparatuses 120, 130, 140 and 150 for testing rotational impact in accordance with some embodiments. The exemplary apparatuses 120, 130, 140 and 150 have the same head models as illustrated in FIGS. 6-9, respectively. As illustrated in FIGS. 10-13, in some embodiments, the at least one impact element 70 includes a rotor 122 coupled with the head model 50 (e.g., through a rod 124) to provide a rotational impact on the head model 50. In some embodiments, a rotational impact is more important than a translational impact because rotational impacts tend to result in more extensive brain injury. The rod 124 may be coupled with the head model 50 and a supporting stand or a bearing system 125 in some embodiments. The bearing system 125 is used to support the skull component 82 allowing the skull component 82 to rotate.

Figure 10:
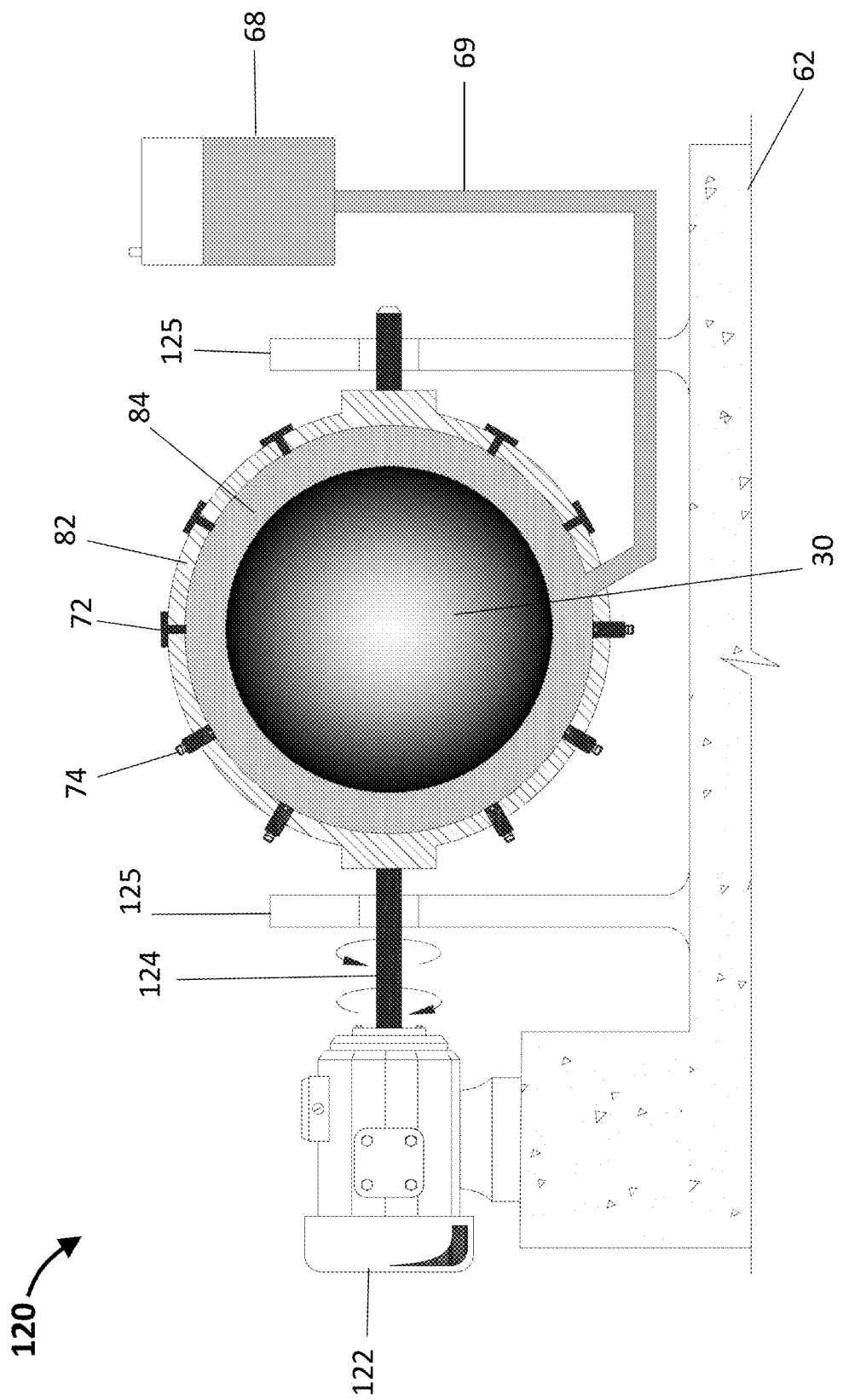
FIG. 10 illustrates an exemplary apparatus including artificial brain in a shape of an inner sphere for testing rotational impact in accordance with some embodiments.

Referring to FIG. 10, the head model 50 is the same as that described in FIG. 6, and comprises an artificial brain component 30 in a spherical shape. A rotational impact plays a significant role in concussive or sub-concussive brain injury. To reveal the intrinsic characteristics of the CSF flow during the rotational impact, an experimental setup is designed with a spherical ball bathed in a liquid environment and enclosed in a container. The rotor 122, which may be run by a motor, is configured to create rotational accelerations/decelerations to the skull component 82, which is further transmitted to the inner sphere via the fluid gap (i.e. the fluid component 84) between the brain component 30 and the skull component 82. The frequency, magnitude and extent (e.g., in terms of amount of rotation) of the rotational impact can be varied. The skull component 82 is transparent to allow direct visualization of the motion of the brain component 30 using a high-speed camera.

Figure 11:
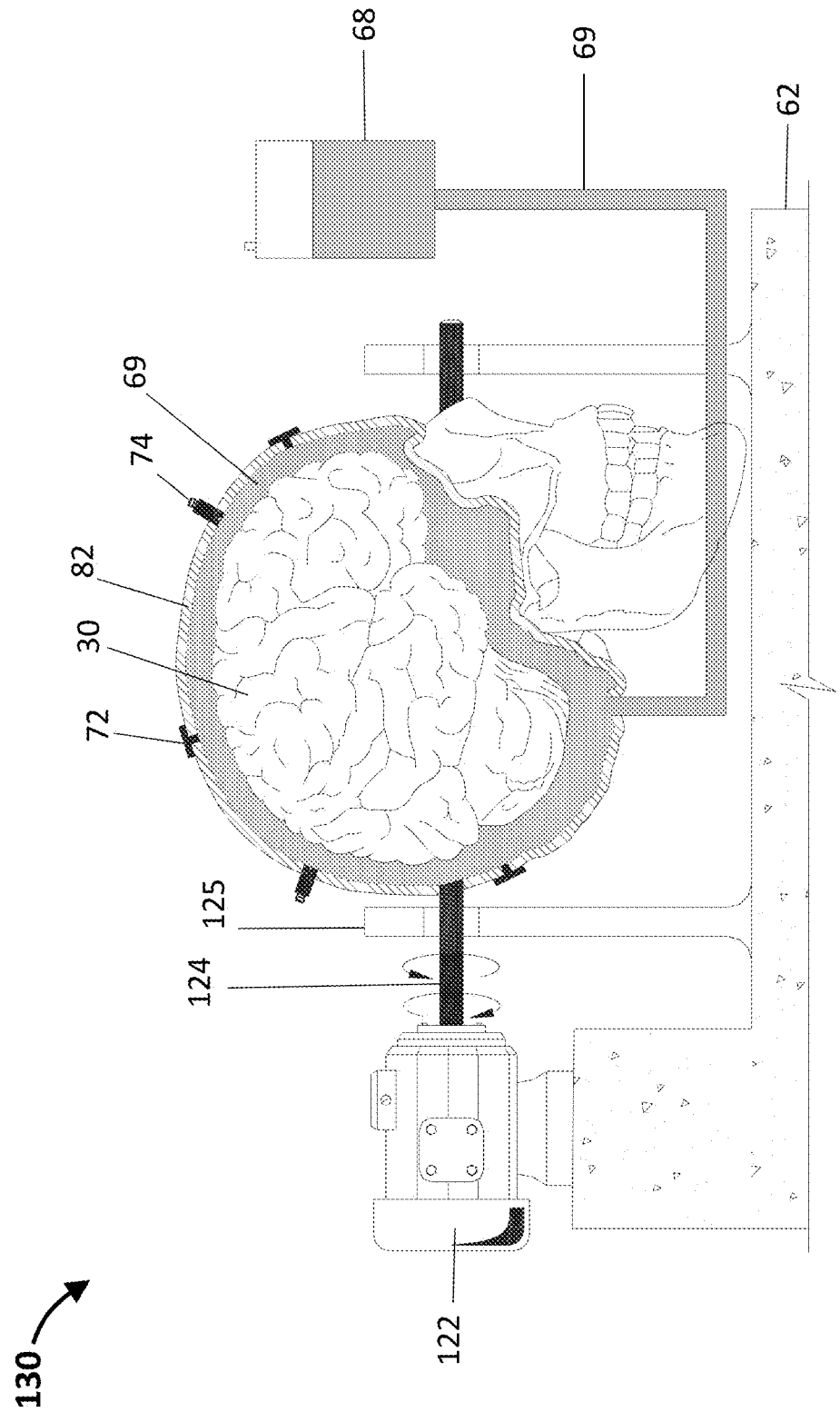
FIG. 11 illustrates an exemplary apparatus including head surrogate for testing rotational impact in accordance with some embodiments.

Referring to FIG. 11, in the apparatus 130, the head model 50 is the same as that described in FIG. 7, and comprises an artificial brain component 30 shaped and sized to simulate a brain of a human subject. The heard model or surrogate is used for testing rotational impact as described in FIG. 10. A biomimetic approach is used to model the rotational impact on the brain surrogate. The apparatus 130 includes a rotor 122 as a rotational impactor and a bearing system 125 as described above. As described in FIGS. 1-4, precise anatomical data from CT scan is used to 3-D print a skull component 82 and to form the negative casting mold for the brain component 30 in some embodiments. A porcine brain can also be used in some embodiments. The apparatus 130 is also instrumented with various sensors as described in FIG. 7. For example, a displacement sensor mounted on the skull component 82 can measure the instantaneous variation of the SAS due to the motion of the brain matter relative to the skull. A gyroscope placed at the location of the medulla oblongata provides data for the angular velocity of the head surrogate. Multiple pressure sensors mounted on the skull component 82 capture the simulated pressure response of the CSF inside the SAS.

Figure 12:
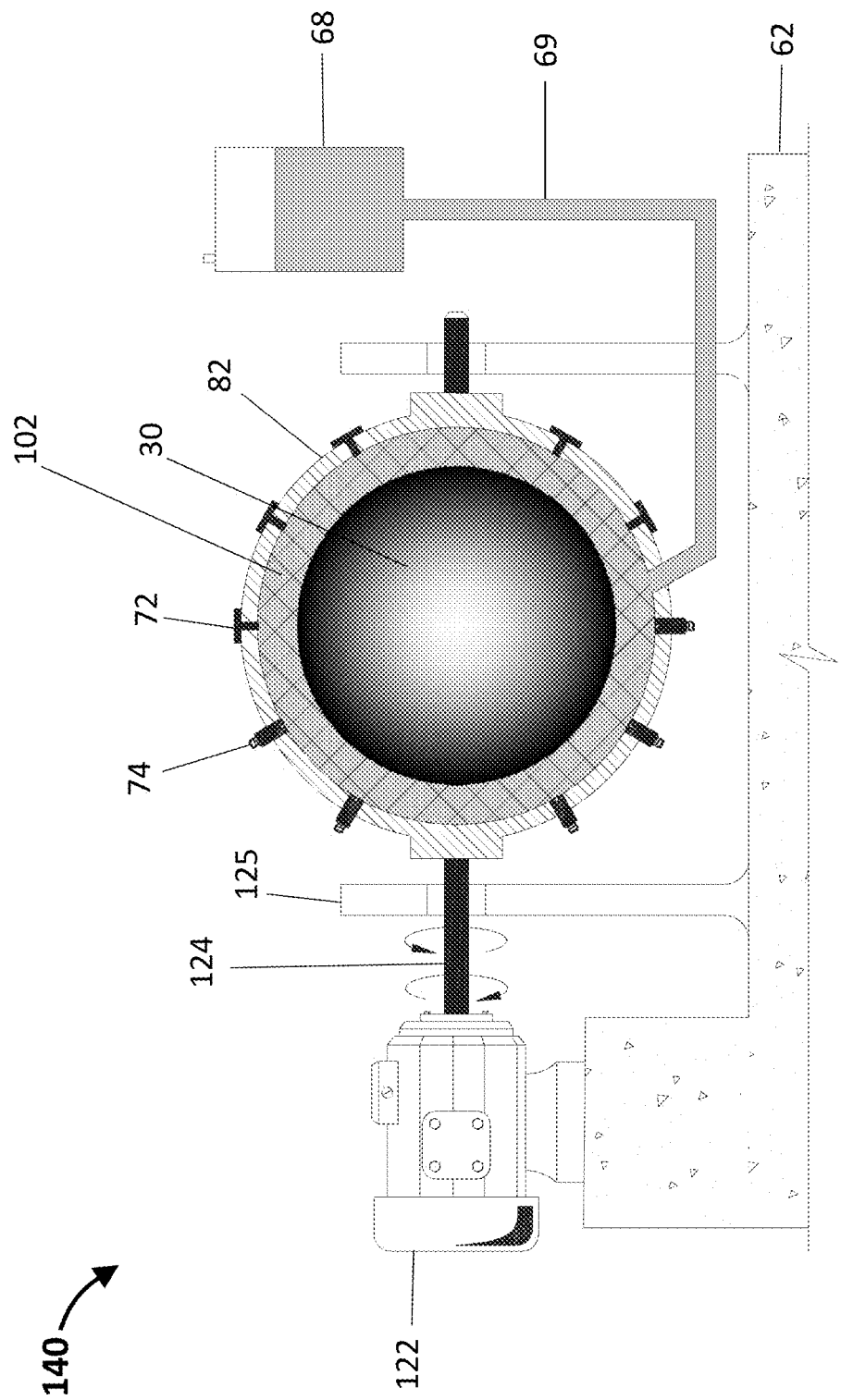
FIG. 12 illustrates an exemplary apparatus including artificial brain in a shape of an inner sphere and porous media for testing rotational impact in accordance with some embodiments.

Referring to FIG. 12, an exemplary apparatus 140 is illustrated. The exemplary apparatus 140 is the same as the exemplary apparatus 120 (FIG. 10) except that the exemplary apparatus 140 includes a layer of porous media 102 for simulating porous arachnoid trabeculae (AT) as described above.

Figure 13:
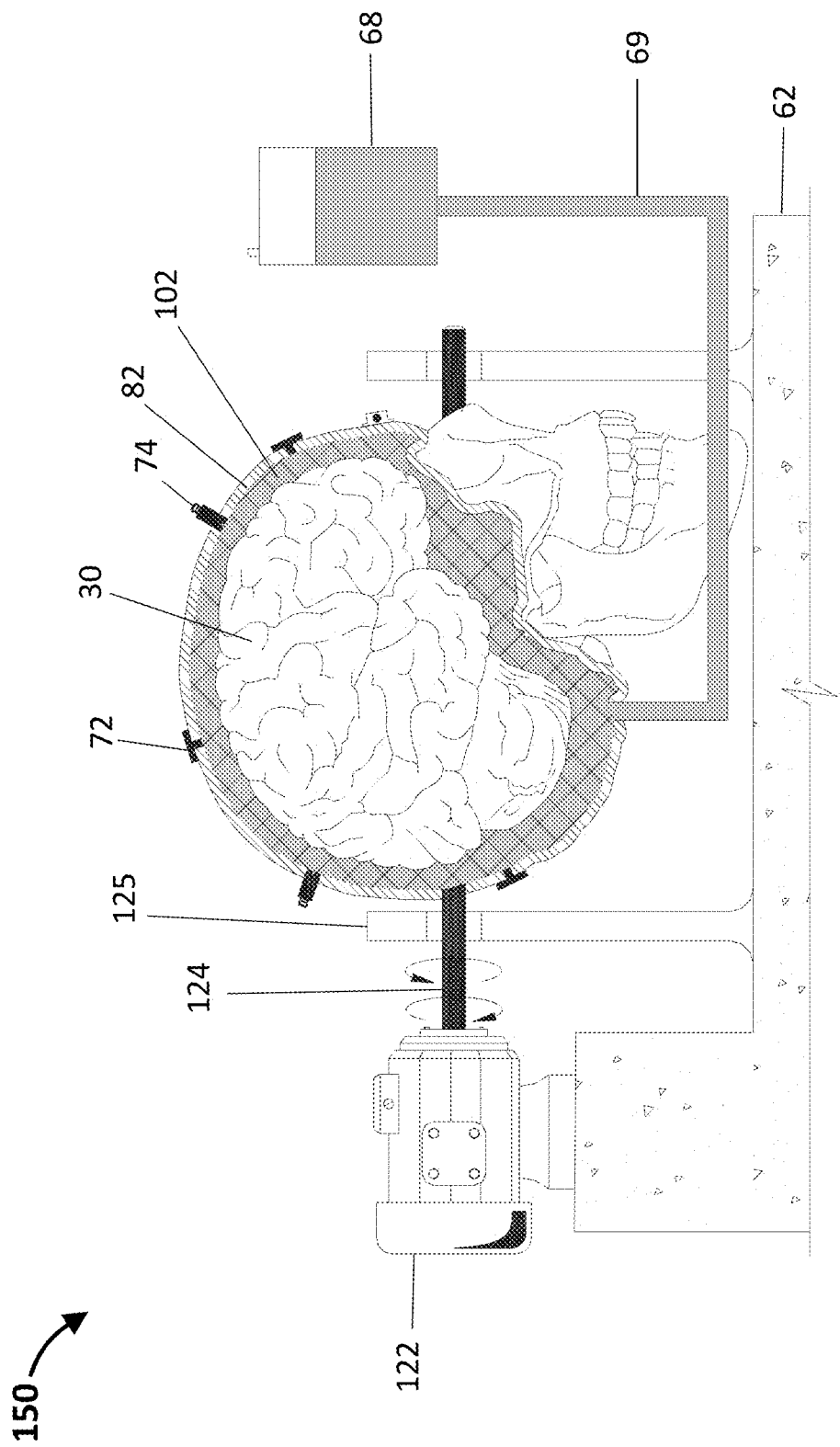
FIG. 13 illustrates an exemplary apparatus including head surrogate having porous media for testing rotational impact in accordance with some embodiments.

Referring to FIG. 13, an exemplary apparatus 150 is illustrated. The exemplary apparatus 150 is the same as the exemplary apparatus 130 (FIG. 10) except that the exemplary apparatus 150 includes a layer of porous media 102 for simulating porous arachnoid trabeculae (AT) as described above.

3. Method of Making and Method of Using the System

FIG. 14 illustrates an exemplary method 300 of making an exemplary system as described in accordance with some embodiments. The method 300 comprises forming a head model, including steps 310, 320, 330, 340 and 350 in FIG. 14 in some embodiments. In step 310, a skull component 82 having a wall defining an interior chamber is provided. At step 320, a brain component 30 is formed. For example, the brain component 30 can be made using the exemplary method 200 as described in FIGS. 1-4.

At step 330, the brain component 30 is placed within the interior chamber or cavity 85. At step 340, a fluid component 84 is supplied into the interior chamber 85. In some embodiments, the method 300 further comprises coupling a fluid tank 68 having the fluid component 84 with the skull component 82 so as to provide the fluid component 84 into the interior chamber 85 with a controlled pressure.

At step 350, in some embodiments, a layer of porous media 102 may be optionally placed between the brain component 30 and the interior wall surface of the skull component 82. In some embodiments, the step of providing a layer of porous media 102 occurs after step 320 and before step 330. Step 350 occurs at the same time as step 330. After the brain component 30 is formed at step 320. The brain component 30 is then coated with porous media 102 and then placed inside the skull component 82. The fluid component 84 is supplied into the interior chamber 85.

At step 360, at least one impact element 70 is provided for giving an impact on the head model. The impact is translational or rotational or both as described above.

FIG. 15 illustrates an exemplary method 400 of using an exemplary system as described for testing impact induced brain trauma in accordance with some embodiments. Referring to FIG. 15, at step 410, an impact on the head model 50 is provided from at least one impact element 70. The impact is translational or rotational or both as described. In some embodiments, in the system such as those described in FIGS. 8-9 and 12-13, the head model 50 may include a layer of porous media 102 disposed between the brain component 30 and the interior wall surface of the skull component 82.

In some embodiments, a rotational impact on the head model 50 is provided by a rotor 122 in the at least one impact element 70. The rotor 122 is coupled with the head model 50.

Referring to FIG. 15, at step 420, data are collected from one or more sensors embedded inside or partially attached with the wall of the skull component or located on a base support. At step 430, a plurality of images are taken using a high speed camera 76 to show one or more components inside the interior chamber 85 before, during and/or after impact. At step 440, the data and the plurality of images are analyzed using a computer and a computer program so as to detect impact induced brain trauma.

The present disclosure provides a good approach to examine the flow and pressurization of the cerebrospinal fluid flow (CSF) in the subarachnoid space (SAS) as the head is exposed to sudden external impacts. The test apparatus or system includes an improved head model to better understand the mechanism of concussive and sub-concussive brain injuries, and to provide guidance for the prevention of such injuries. For example, the CSF flow through the soft, porous arachnoid trabeculae (AT) in the SAS, and both translational and rotational impact are considered. With consideration of the complicated nature of the biological system, a biomimetic approach is used to investigate the mechanism of brain injury with more and better results.

The systems and the methods in the present disclosure are useful, for example, in studying patient-specific pathology and designing products such as helmets to protect heads. For example, the apparatuses and the methods of the present disclosure can be used to provide predictable results in locating the potential areas having brain injury. The brain component can be patient-specific based on CT scan data. The apparatus and the methods provide a cost-saving alternative to expensive magnetic resonance imaging (MM). When a specific area for injury is identified, an MM can be used for further diagnosis. As another example, the apparatus and the methods in the present disclosure can be used for designing helmets or other head-protection products. Such a product can be placed on a head model as described herein, and impact testing can be performed. The results provide guidance for designing better products to minimize or eliminate brain injury.

A computer implemented program can be developed and used for collecting and analyzing the data and images. The methods and system described herein may be at least partially embodied in the form of computer-implemented processes and apparatus for practicing those processes. The disclosed methods may also be at least partially embodied in the form of tangible, non-transient machine readable storage media encoded with computer program code. The media may include, for example, RAMs, ROMs, CD-ROMs, DVD-ROMs, BD-ROMs, hard disk drives, flash memories, or any other non-transient machine-readable storage medium, or any combination of these mediums, wherein, when the computer program code is loaded into and executed by a computer, the computer becomes an apparatus for practicing the method. The methods may also be at least partially embodied in the form of a computer into which computer program code is loaded and/or executed, such that, the computer becomes an apparatus for practicing the methods. When implemented on a general-purpose processor, the computer program code segments configure the processor to create specific logic circuits. The methods may alternatively be at least partially embodied in a digital signal processor formed of application specific integrated circuits for performing the methods.

Although the subject matter has been described in terms of exemplary embodiments, it is not limited thereto. Rather, the appended claims should be construed broadly, to include other variants and embodiments, which may be made by those skilled in the art.

What is claimed is:

1. A system for testing impact induced brain trauma, comprising:
   a head model comprising:
      a skull component having a wall defining an interior chamber, the wall comprising an exterior wall surface and an interior wall surface;
      a brain component disposed within the interior chamber, the brain component comprising a gel material for simulating brain tissue;
      a fluid component disposed inside the interior chamber; and
      a layer of porous media disposed between the brain component and the interior wall surface of the skull component, wherein the layer of porous media comprises a polymer, and the fluid component is disposed inside the layer of porous media.

2. The system of claim 1, wherein the skull component is made of a rigid and transparent material.

3. The system of claim 1, wherein the brain component is in a spherical shape, or is shaped and sized to simulate a brain of a human subject.

4. The system of claim 1, further comprising a tank fluidly coupled with the skull component and configured to provide the fluid component into the interior chamber.

5. The system of claim 4, wherein the tank is connected with the skull component through a tube and configured to adjust a pressure of the fluid component inside the interior chamber.

6. The system of claim 1, further comprising:
   at least one impact element configured to provide an impact on the head model, the impact being translational or rotational or both.

7. The system of claim 6, wherein the at least one impact element comprises a rotor coupled with the head model to provide a rotational impact on the head model.

8. The system of claim 1, further comprising one or more sensors embedded inside the wall of the skull component.

9. The system of claim 8, wherein the one or more sensors are selected from the group consisting of a pressure sensor, a displacement sensor, an accelerometer, and a combination thereof.

10. The system of claim 8, further comprising a camera configured to take a plurality of images showing one or more components inside the interior chamber.

11. The system of claim 10, further comprising a computer configured to analyze data from the one or more sensors and the plurality of images for detecting impact induced brain trauma.

12. A system for testing impact induced brain trauma, comprising:
   a head model comprising:
      a skull component having a wall defining an interior chamber, the wall comprising an exterior wall surface and an interior wall surface;
      a brain component disposed within the interior chamber, the brain component comprising a gel material for simulating brain tissue;
      a fluid component disposed inside the interior chamber; and
      a layer of porous media disposed between the brain component and the interior wall surface of the skull component, wherein the layer of porous media comprises a polymer, and the fluid component is disposed inside the layer of porous media; and
   a tank fluidly coupled with the skull component and configured to adjust a pressure of the fluid component inside the interior chamber.

13. The system of claim 12, wherein the skull component is made of a rigid and transparent material, and the brain component is in a spherical shape, or is shaped and sized to simulate a brain of a human subject.

14. The system of claim 1, wherein the tank is configured to provide the fluid component into the interior chamber.

15. A method of forming a system of claim 1, comprising forming a head model, wherein forming the head model comprises:
   providing the skull component;
   forming the brain component;
   placing the brain component within the interior chamber; and
   placing the layer of porous media between the brain component and the interior wall surface of the skull component.

16. The method of claim 15, further comprising
   coupling a tank disposed outside the skull component, wherein the tank is fluidly coupled with the skull component configured to supply the fluid component into the interior chamber, and adjust a pressure of the fluid component inside the interior chamber through the tank.

17. The method of claim 15, further comprising:
   providing at least one impact element configured to provide an impact on the head model, the impact being translational or rotational or both.

18. A method of using a system for testing impact induced brain trauma, the system comprising:
   a head model comprising:
      a skull component having a wall defining an interior chamber, the wall comprising an exterior wall surface and an interior wall surface;
      a brain component disposed within the interior chamber, the brain component comprising a gel material for simulating brain tissue;
      a fluid component disposed inside the interior chamber; and
      a layer of porous media disposed between the brain component and the interior wall surface of the skull component, wherein the layer of porous media comprises a polymer, and the fluid component is disposed inside the layer of porous media,
   wherein the method comprises a step of providing an impact on the head model from at least one impact element, the impact being translational or rotational or both.

19. The method of claim 18, further comprising
   supplying the fluid component into the interior chamber from a tank disposed outside the skull component and fluidly coupled with the skull component; and
   adjusting a pressure of the fluid component inside the interior chamber through the tank.

20. The method of claim 19, further comprising:
   collecting data from one or more sensors embedded inside the wall of the skull component;
   taking a plurality of images through a camera to show one or more components inside the interior chamber; and
   analyzing the data and the plurality of images using a computer so as to detect impact induced brain trauma.

* * * * *